(12) United States Patent
Row et al.

(10) Patent No.: US 12,322,124 B2
(45) Date of Patent: Jun. 3, 2025

(54) METHODS AND SYSTEMS FOR PERFORMING IMAGE REGISTRATION IN A COMPUTER-ASSISTED SURGERY SYSTEM

(71) Applicant: Mobius Imaging, LLC, Shirley, MA (US)

(72) Inventors: Gordon Row, Groton, MA (US); Kyle Schwartz, Somerville, MA (US); Stephen Lang, Hollis, NH (US); Edward Daley, Maynard, MA (US)

(73) Assignee: Mobius Imaging, LLC, Shirley, MA (US)

( * ) Notice: Subject to any disclaimer, the term of this patent is extended or adjusted under 35 U.S.C. 154(b) by 286 days.

(21) Appl. No.: 17/918,753

(22) PCT Filed: Apr. 14, 2021

(86) PCT No.: PCT/US2021/027181
§ 371 (c)(1),
(2) Date: Oct. 13, 2022

(87) PCT Pub. No.: WO2021/211650
PCT Pub. Date: Oct. 21, 2021

(65) Prior Publication Data
US 2023/0133825 A1      May 4, 2023

Related U.S. Application Data

(60) Provisional application No. 63/009,622, filed on Apr. 14, 2020.

(51) Int. Cl.
*G06T 7/33*       (2017.01)
*A61B 34/20*      (2016.01)
(Continued)

(52) U.S. Cl.
CPC ............... *G06T 7/33* (2017.01); *A61B 34/20* (2016.02); *A61B 34/32* (2016.02); *A61B 90/39* (2016.02);
(Continued)

(58) Field of Classification Search
CPC . A61B 34/20; A61B 90/39; A61B 2090/3966; A61B 2090/3937; A61B 2090/3995
See application file for complete search history.

(56) References Cited

U.S. PATENT DOCUMENTS 5,368,030 A * 11/1994 Zinreich ................ A61B 90/39
                                                           324/309
5,394,457 A *  2/1995 Leibinger .............. A61B 90/39
                                                           378/162

(Continued)

OTHER PUBLICATIONS

International Search Report for Application No. PCT/US2021/027181 dated Jul. 28, 2021, 1 page.

*Primary Examiner* — Keith M Raymond
*Assistant Examiner* — Johnathan Maynard
(74) *Attorney, Agent, or Firm* — Howard & Howard Attorneys PLLC

(57) ABSTRACT

A surgical system including a patient tracker and a tracking system. The patient tracker is adapted for attachment to a patient, and includes a hybrid marker having a radiological marker contained within an optical marker. The tracking system tracks the hybrid marker. A computing device obtains a three-dimensional image of a patient's anatomy and the attached patient tracker; identifies a three-dimensional portion of the hybrid marker within a scan volume; determines a location of the hybrid marker within the scan volume based on the identified three-dimensional portion; tracks the location of the hybrid marker in three-dimensional space using the tracking system while the patient tracker remains fixed to the patient; and registers the three-dimen- (Continued)

sional image in three-dimensional space based on a known geometric relationship between the location of the hybrid marker within the scan volume and the location of the hybrid marker in three-dimensional space.

18 Claims, 11 Drawing Sheets

(51) Int. Cl.
    *A61B 34/32*     (2016.01)
    *A61B 90/00*     (2016.01)
    *B25J 9/16*     (2006.01)
    *G06T 7/73*     (2017.01)

(52) U.S. Cl.
    CPC ............... B25J 9/1664 (2013.01); G06T 7/73 (2017.01); *A61B 2034/2055* (2016.02); *A61B 2090/3937* (2016.02); *A61B 2090/3966* (2016.02); *A61B 2090/3995* (2016.02); *G06T 2207/10028* (2013.01); *G06T 2207/20221* (2013.01); *G06T 2207/30004* (2013.01); *G06T 2207/30196* (2013.01); *G06T 2207/30204* (2013.01)

(56) References Cited

U.S. PATENT DOCUMENTS

| | | | |
|---|---|---|---|
| 5,469,847 A * | 11/1995 | Zinreich | .................. H05G 1/26 324/309 |
| 6,341,231 B1 | 1/2002 | Ferre et al. | |
| 6,662,036 B2 | 12/2003 | Cosman | |
| 8,118,488 B2 | 2/2012 | Gregerson | |
| 8,662,684 B2 | 3/2014 | Shafer et al. | |
| 9,486,295 B2 | 11/2016 | Vilsmeier et al. | |
| 11,103,990 B2 | 8/2021 | Sebring et al. | |
| 2001/0004395 A1 | 6/2001 | McCrory et al. | |
| 2004/0075048 A1* | 4/2004 | Zyromski | ............... A61B 6/583 250/493.1 |
| 2005/0020916 A1* | 1/2005 | MacFarlane | ........... A61B 90/39 600/431 |
| 2005/0228256 A1 | 10/2005 | Labadie et al. | |
| 2010/0063388 A1* | 3/2010 | Solar | ..................... A61B 90/39 600/426 |
| 2011/0105896 A1* | 5/2011 | Zagorchev | ............ A61B 90/39 427/2.12 |
| 2012/0059244 A1* | 3/2012 | McClelland | ............ A61B 6/12 424/9.4 |
| 2013/0135732 A1* | 5/2013 | Shafer | .................... G01T 1/2014 359/545 |
| 2013/0135736 A1 | 5/2013 | Shafer et al. | |
| 2013/0267829 A1* | 10/2013 | Ojha | ..................... A61B 6/032 250/336.1 |
| 2014/0003572 A1 | 1/2014 | Gregerson et al. | |
| 2014/0139215 A1 | 5/2014 | Gregerson et al. | |
| 2014/0265182 A1 | 9/2014 | Stanton et al. | |
| 2014/0275953 A1 | 9/2014 | Gregerson et al. | |
| 2015/0011861 A1* | 1/2015 | Rahmer | ................. A61B 90/39 600/409 |
| 2016/0267659 A1* | 9/2016 | Vasey | .................... A61B 90/39 |
| 2016/0303083 A1* | 10/2016 | Dibas | ................. A61K 31/4174 |
| 2017/0071667 A1* | 3/2017 | Leung | .................... A61B 90/39 |
| 2017/0188880 A1* | 7/2017 | Sela | ...................... G16H 40/63 |
| 2022/0117682 A1* | 4/2022 | Malackowski | ........ A61B 34/70 |

* cited by examiner

METHODS AND SYSTEMS FOR PERFORMING IMAGE REGISTRATION IN A COMPUTER-ASSISTED SURGERY SYSTEM

RELATED APPLICATIONS

The subject patent application claims priority to and all the benefits of U.S. Provisional Patent Application No. 63/009,622, filed on Apr. 14, 2020, which is hereby incorporated herein by reference in its entirety.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s)) in the surgical area. These procedures may be used to aid the surgeon in planning a surgical procedure and may also provide the surgeon with relevant feedback during the course of surgical procedure.

The image registration process involves several steps to make a connection between the virtual 3D scan and the physical patient. The term "registration" in this context refers to the process by which visible or physical landmarks on the patient are spatially coordinated with a detailed pre-operative scan (e.g., an x-ray computed tomography (CT) or magnetic resonance (MR) imaging scan). One approach that has been used for image registration in image guided surgery is an optical method of registration in which the imaging device (i.e., scanner) and a patient reference array are simultaneously tracked at the onset of an imaging scan. This establishes a relative position, in six dimensions (6D) between the patient and the scan. Other technologies use radiological markers of known dimensions introduced into a 2D or 3D scan and used to locate the patient with respect to the scan.

Existing methods for image registration may introduce significant sources of error that tend to limit the overall system accuracy. There is a continuing need for improvements in image registration for computer-assisted surgical procedures.

SUMMARY

The present disclosure provides a surgical system including a patient tracker and a motion tracking system. The patient tracker is adapted for attachment to a patient, and includes at least one hybrid marker having a radiological marker contained within an optical marker. The motion tracking system is configured for tracking a location of the at least one hybrid marker. A computing device is configured to: obtain a three-dimensional image of a patient's anatomy and the patient tracker attached to the patient; identify a three-dimensional portion of the hybrid marker within a scan volume of the three-dimensional image; determine a location of the hybrid marker within the scan volume based on the identified three-dimensional portion of the hybrid marker; track the location of the hybrid marker in three-dimensional space using the motion tracking system while the patient tracker remains fixed to the patient; and register the three-dimensional image of the patient's anatomy in three-dimensional space based on a known geometric relationship between the location of the hybrid marker within the scan volume and the location of the hybrid marker in three-dimensional space.

The present disclosure also provides a method of registering patient images in a surgical system, the method including: obtaining a three-dimensional image of a patient's anatomy and a patient tracker attached to the patient, the patient tracker including at least one hybrid marker having a radiological marker contained within an optical marker; identifying a three-dimensional portion the hybrid marker within a scan volume of the three-dimensional image; determining a location of the hybrid marker within the scan volume based on the identified three-dimensional portion of the hybrid marker; tracking the location of the hybrid marker in three-dimensional space using the motion tracking system while the patient tracker remains fixed to the patient; and registering the three-dimensional image of the patient's anatomy in three-dimensional space based on a known geometric relationship between the location of the hybrid marker within the scan volume and the location of the hybrid marker in three-dimensional space.

The present disclosure also provides a method of registering patient images in a computer-assisted surgery system, including: obtaining a three-dimensional image of a patient's anatomy and an optical marker having a body while the optical marker is fixed to the patient; identifying a three-dimensional surface of the body of the optical marker within a scan volume of the three-dimensional image; determining a location of the optical marker within the scan volume based on the identified three-dimensional surface of the body; tracking the location of the optical marker in three-dimensional space using the motion tracking system while the optical marker remains fixed to the patient; and registering the three-dimensional image of the patient's anatomy in three-dimensional space based on a known geometric relationship between the location of the optical marker within the scan volume and the location of the optical marker in three-dimensional space.

The present disclosure also provides computer-assisted surgery system, including an optical marker having a body, and a motion tracking system for tracking a location of the optical marker. A computing device is configured to: obtain a three-dimensional image of a patient's anatomy and the optical marker while the optical marker is fixed to the patient; identify a three-dimensional surface of the body of the optical marker within a scan volume of the three-dimensional image; determine a location of the optical marker within the scan volume based on the identified three-dimensional surface of the body; track the location of the optical marker in three-dimensional space using the motion tracking system while the optical marker remains fixed to the patient; and register the three-dimensional image of the patient's anatomy in three-dimensional space based on a known geometric relationship between the location of the optical marker within the scan volume and the location of the optical marker in three-dimensional space.

The present disclosure also provides a method of registering patient images in a computer-assisted surgery system, including obtaining a three-dimensional image of a patient's anatomy and a patient tracker attached to the patient, the patient tracker including at least one radiological marker and at least one second marker; identifying a location of the at least one radiological marker of the patient tracker within a scan volume of the three-dimensional image; tracking a pose of the at least one second marker of the patient tracker in three-dimensional space using the motion tracking system while the patient tracker remains attached to the patient; and registering the three-dimensional image of the patient's anatomy in three-dimensional space based on a known geometric relationship between the at least one radiological marker and the at least one second marker of the patient tracker.

The present disclosure also provides a computer-assisted surgery system, including a motion tracking system, and a patient tracker including at least one radiological marker and at least one second marker and configured to attach to a patient a motion tracking system. A computing device is configured to: obtain a three-dimensional image of a patient's anatomy and the patient tracker; identify a location of the at least one radiological marker of the patient tracker within a scan volume of the three-dimensional image; track a pose of the at least one second marker of the patient tracker in three-dimensional space using the motion tracking system while the patient tracker remains attached to the patient; and register the three-dimensional image of the patient's anatomy in three-dimensional space based on a known geometric relationship between the at least one radiological marker and the at least one second marker of the patient tracker.

The present disclosure also provides a method of registering patient images in a computer-assisted surgery system, including: obtaining a three-dimensional image of a patient's anatomy and a primary patient tracker attached to a first anatomic structure of the patient and a secondary patient tracker attached to a second anatomic structure of the patient, the primary patient tracker including at least one radiological marker and at least one second marker, and the secondary patient tracker including at least one radiological marker; identifying locations of the radiological markers within a scan volume of the three-dimensional image; tracking a pose of the at least one second marker of the primary patient tracker in three-dimensional space using the motion tracking system while the primary patient tracker remains attached to the first anatomic structure; registering the three-dimensional image of the patient's anatomy in three-dimensional space based on a known geometric relationship between the at least one radiological marker and the at least one second marker of the primary patient tracker; monitoring the pose of the secondary patient tracker by tracking a tracked instrument located adjacent to the secondary patient tracker in three-dimensional space using the motion tracking system to determine whether the second anatomic structure has moved relative to the first anatomic structure; and providing feedback to a user of the computer-assisted surgery system based on a determination of movement of the second anatomic structure relative to the first anatomic structure.

The present disclosure also provides a computer-assisted surgery system, including a patient marker system, a tracked instrument, and a motion tracking system. The patient marker system includes: a primary patient tracker having at least one radiological marker, and at least one second marker and configured to attach to a first anatomic structure of a patient; and a secondary patient tracker having at least one radiological marker and configured to attach to a second anatomic structure of the patient. The motion tracking system is configured to track the primary patient tracker and the instrument. A computing device is configured to: obtain a three-dimensional image of a patient's anatomy and the primary patient tracker and the secondary patient tracker; identify locations of the radiological markers within a scan volume of the three-dimensional image; track a pose of the at least one second marker of the primary patient tracker in three-dimensional space using the motion tracking system while the primary patient tracker remains attached to the first anatomic structure; register the three-dimensional image of the patient's anatomy in three-dimensional space based on a known geometric relationship between the at least one radiological marker and the at least one second marker of the primary patient tracker; monitor the pose of the secondary patient tracker by tracking a tracked instrument located adjacent to the secondary patient tracker in three-dimensional space using the motion tracking system to determine whether the second anatomic structure has moved relative to the first anatomic structure; and provide feedback to a user of the computer-assisted surgery system based on a determination of movement of the second anatomic structure relative to the first anatomic structure.

The present disclosure also provides a patient marker system, including: a primary patient tracker having at least one radiological marker and at least one second marker and configured to attach to a first anatomic structure of a patient; and a secondary patient tracker having at least one radiological marker and a touchpoint and configured to attach to a second anatomic structure of the patient.

The present disclosure also provides a surgical system, including a patient tracker adapted for attachment to a patient, the patient tracker including at least one hybrid marker having a radiological marker contained within an optical marker; a motion tracking system for tracking a location of the at least one hybrid marker; an imaging device configured to perform a scan of the patient while the patient tracker is attached to the patient; and a computing device. The computing device is configured to: obtain a three-dimensional image of a patient's anatomy and the patient tracker attached to the patient; identify a three-dimensional portion of the hybrid marker within a scan volume of the three-dimensional image; determine a location of the hybrid marker within the scan volume based on the identified three-dimensional portion; track the location of the hybrid marker in three-dimensional space using the motion tracking system while the patient tracker remains fixed to the patient; and register the three-dimensional image of the patient's anatomy in three-dimensional space based on a known geometric relationship between the location of the hybrid marker within the scan volume and the location of the hybrid marker in three-dimensional space.

The present disclosure also provides surgical system, including: a patient tracker adapted for attachment to a patient, the patient tracker including at least one hybrid marker having a radiological marker contained within an optical marker; and a surgical robot including a robotic arm and an end effector. The robotic arm includes a robot tracker attached to the robotic arm. A motion tracking system tracks a location of the at least one hybrid marker and a location of the robot tracker. An imaging device is configured to perform a three-dimensional image scan of the patient while the patient tracker is attached to at least one anatomical feature of the patient. A computing device is configured to: track the location of the hybrid marker in three-dimensional space using the motion tracking system while the patient tracker remains attached to the patient; track the location of the robot tracker in three-dimensional space using the motion tracking system while the robot track remains attached to the robotic arm; monitor a pose of the robotic arm by tracking the robot tracker in three-dimensional space using the motion tracking system to determine whether the robot tracker moved relative to the hybrid marker; and adjust the pose of the robotic arm based on a determination of a movement of the robot tracker relative to at least one of anatomical feature and hybrid marker.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various examples will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various examples relate to methods and systems for performing computer-assisted surgery, and in particular, to methods and systems for performing image registration in computer-assisted surgery. Computer-assisted surgery may include techniques in which surgical instruments or other equipment are tracked in space and, through various technologies and software programs, correlated to a "virtual" three-dimensional dataset that includes portions of a patient's anatomy. The "virtual" three-dimensional dataset may be obtained using pre-operative medical imaging, intra-operative medical imaging, or both (e.g., x-ray computed tomography (CT); magnetic resonance (MR) imaging; ultrasound imaging, etc.). in some examples, computer-assisted surgical procedures may include image guided surgery and robotic surgery. The term "image registration" in this context may refer to the process by which visible or physical landmarks on the patient are spatially coordinated with the "virtual" three-dimensional dataset, such as a detailed CT and MR scans.

Figure 1:
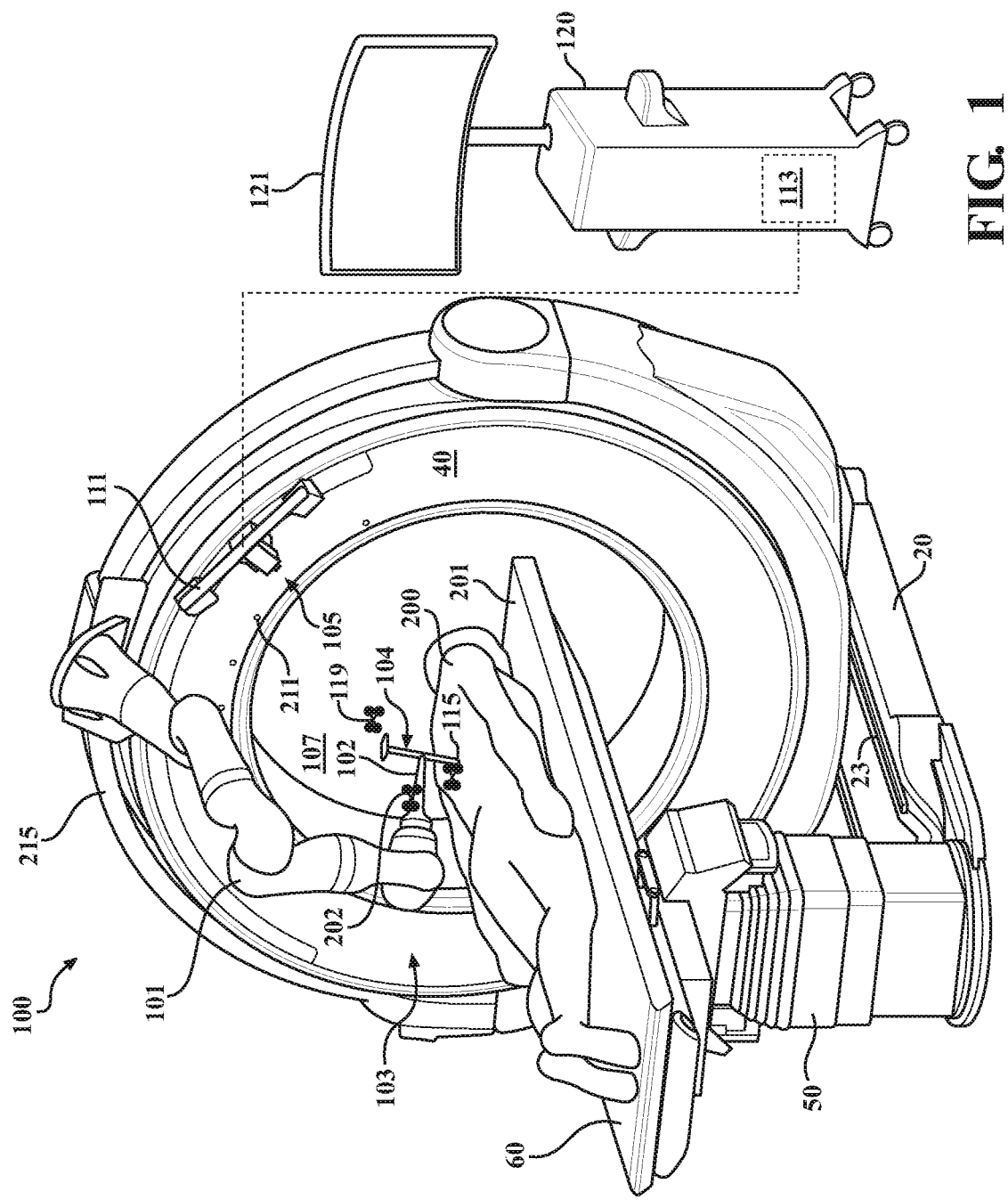
FIG. 1 is a perspective view of a system for performing robotically-assisted image-guided surgery.

FIG. 1 illustrates a surgical system 100 configured to perform computer assisted surgery. The surgical system may include robotically-assisted image-guided surgery according to various examples. The surgical system 100, in this example, generally includes an imaging device 103, a motion tracking system 105, and a robotic arm 101, as well as one or more computing devices (also referred to herein as "computers") for performing a robotically-assisted surgical procedure. In other examples, the surgical system may include an imaging device 103 and a motion tracking system 105 and may be used for performing an image-guided surgical procedure.

The surgical system 100 may include a robotic arm 101. The robotic arm 101 may comprise a multi-joint arm that includes a plurality of linkages connected by joints having actuator(s) to enable the linkages to rotate, bend and/or translate relative to one another in response to control signals from a robot control system, which may include, define, or otherwise employ one or more computing devices, computers, and/or controllers for operating the robotic arm 101. The robotic arm may include encoders at one or more of the joints. The robotic arm 101 may be fixed to a support structure at one end and may have an end effector 102 at the other end of the robotic arm 101.

The surgical system 100 includes an imagining device 103. The imaging device 103 may be used to obtain diagnostic images of a patient 200, which may be a human or animal patient. In some examples, the imaging device 103 may be an x-ray computed tomography (CT) imaging device. The patient 200 may be positioned within a central bore 107 of the imaging device 103 and an x-ray source, and a detector may be rotated around the bore 107 to obtain x-ray image data (e.g., raw x-ray projection data) of the patient 200. The collected image data may be processed using one or more computing devices, computers, processors, and/or controllers (e.g., computing device 113, 201, 1300) to perform a three-dimensional reconstruction of the object. Those having ordinary skill in the art will appreciate that one or more of the computing devices referred to herein may include or otherwise be realized by one or more discrete controllers, processors, computers, cloud-based computing devices, handheld computing devices, servers, tablet computers, smartphones, pendant controllers, cellular telephones, the like, and/or combinations thereof. In some examples, the computing device may be realized by a controller or multiple controllers configured individually or networked together to direct imaging, process image reconstruction, robotic control, tracking, or a combination thereof. In other examples, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In some examples, image data may be obtained pre-operatively (i.e., prior to performing a surgical procedure), intra-operatively (i.e., during a surgical procedure), or both by positioning the patient 200 within the bore 107 of the imaging device 103. In the surgical system 100 of FIG. 1, this may be accomplished by moving the imaging device 103 over the patient 200 to perform a scan while the patient 200 may remain stationary.

Examples of x-ray CT imaging devices that may be used according to various examples are described in, for example, U.S. Pat. No. 8,118,488, U.S. Patent Application Publication No. 2014/0139215, United States Patent Application Publication No. 2014/0003572, United States Patent Application Publication No. 2014/0265182 and United States Patent Application Publication No. 2014/0275953, the entire contents of all of which are incorporated herein by reference. In the example shown in FIG. 1, the patient support 60 (e.g., surgical table) upon which the patient 200 may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient 200, and may translate away from the patient 200 to an out-of-the-way position for performing a surgical procedure on the patient 200.

An example imaging device 103 that may be used is the AIRO® intra-operative CT system manufactured by Mobius Imaging, LLC. Other imaging devices may also be utilized. For example, the imaging device 103 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-arm® surgical imaging system form Medtronic, plc. The imaging device 103 may also be a C-arm x-ray fluoroscopy device. In other examples, the imaging device 103 may be a fixed-bore imaging device, and the patient 200 may be moved into the bore of the device, either on a surgical support 60 as shown in FIG. 1, or on a separate patient table that is configured to slide in and out of the bore. Further, although the imaging device 103 shown in FIG. 1 is located close to the patient 200 within the surgical theater, the imaging device 103 may be located remote from the surgical theater, such as in another room or building (e.g., in a hospital radiology department).

The surgical system 100 includes a motion tracking system 105 (also referred to as a "navigation system" or "tracking system"). The motion tracking system 105 shown in FIG. 1 may include a plurality of marker devices 119, 202, 115. The marker devices 119, 202, 115 may also be referred to as trackers 119, 202, 115. The motion tracking system 105 further includes an optical sensing device 111 (herein known as the optical sensing device; localizer 111), which is described further below. Various systems and technologies exist for tracking the position (including location and/or orientation) of objects as they move within a three-dimensional space. Such tracking systems may include a plurality of active and/or passive markers fixed to the object(s) to be tracked. In some examples, the markers are fixed to the trackers and tracked using a sensing device capable of detecting radiation emitted by, or reflected from the markers. A 3D model of the space may be constructed in software based on the signals detected by the localizer 111.

The motion tracking system 105 in the example of FIG. 1 includes a plurality of trackers 119, 202 and 115 and a stereoscopic localizer 111. The localizer 111 may include two or more cameras (e.g., IR cameras, visible light cameras, or both). The motion tracking system 105 may include, define, or otherwise employ one or more computing devices, computers, and/or controllers. The localizer 111 may include one or more radiation sources (e.g., diode ring(s)) that direct radiation (e.g., IR radiation) into the surgical field, where the radiation may be reflected by the marker devices 119, 202 and 115 and received by the cameras of the localizer 111. The trackers 119, 202, 115 may each include three or more (e.g., four) markers. In some examples, the markers may be passive markers including reflecting spheres which the motion tracking system 105 may use to construct a coordinate system for each of the trackers 119, 202 and 115. In other examples, described further below, the trackers 119, 202, 115 may include active markers. In further examples, the trackers 119, 202, 115 may include a combination of the active and passive markers. In some examples, described further below, a passive marker may be disposed within an active marker. A computing device 113 may be coupled to the localizer 111 and may determine the transformations between each of the trackers 119, 202, 115 and the cameras using, for example, triangulation techniques. A 3D model of the surgical space in a common coordinate system may be generated and continually updated using motion tracking software implemented by the computing device 113. In some examples, the computing device 113 may also receive image data from the imaging device 103 and may register the image data to the common coordinate system as the motion tracking system 105 using an image registration technique as described further below. In some examples, the patient tracker 115 (e.g., a patient reference array) may be rigidly attached to a landmark in the anatomical region of interest (e.g., clamped or otherwise attached to a bony portion of the patient's anatomy) to enable the anatomical region of interest to be continually tracked by the motion tracking system 105. Additional trackers 119 may be attached to surgical tools 104 to enable the tools 104 to be tracked within the common coordinate system. When performing robot-assisted surgery, the additional tracker 202 may be rigidly attached to the robotic arm 101, such as on the end effector 102 of the robotic arm 101, to enable the position of robotic arm 101 and end effector 102 to be tracked using the motion tracking system 105. The computing device 113 may also include software configured to perform a transform between the joint coordinates of the robotic arm 101 and the common coordinate system of the motion tracking system 105, which may enable the pose of the end effector 102 of the robotic arm 101 to be controlled with respect to the patient 200.

It should be understood that the combination of position and orientation of an object is referred to as the pose of the object. Throughout this disclosure, it is contemplated that the term pose may be replaced by position and/or orientation and vice-versa to achieve suitable examples of the concepts described herein.

The motion tracking system 105 may utilize active markers. Active markers may include radiation emitters (e.g., LEDs) that may emit radiation that is detected by the localizer 111. Each active marker or sets of active markers attached to a particular object by a tracker may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active markers may be fixed relative to the patient 200, such as secured to the patient's skin via an adhesive membrane or mask. Additional active markers may be fixed to surgical tools 104 and/or to the end effector 102 of the robotic arm 101 to allow these objects to be tracked relative to the patient 200.

In further examples, the passive markers on the trackers may include moiré patterns that may enable their pose to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria Innovation Inc. of Milwaukee, Wisconsin. Other tracking technologies, such as computer vision systems and/or magnetic-based tracking systems, may also be utilized.

The surgical system 100 may also include a display device 121 as schematically illustrated in FIG. 1. The display device 121 may display image data of the patient's anatomy obtained by the imaging device 103. The display device 121 may facilitate planning for a surgical procedure, such as by enabling a surgeon to select one or more target positions in the patient's body and/or a path or trajectory into the patient's body for inserting surgical tool(s) and/or implants to a target position while minimizing damage to other tissue or organs of the patient. The pose of one or more objects tracked by the motion tracking system 105 may be shown on the display 121, and may be shown overlaying the image data. In the example of FIG. 1, the display 121 is located on a mobile cart 120. A computing device 113 for controlling the operation of the display 121 may also be housed within the cart 120. In some examples, the computing device 113 may be coupled to the localizer 111 and may also perform all or a portion of the processing (e.g., tracking calculations) for the motion tracking system 105. In some examples, one or more separate computers or computing devices may perform the motion tracking processing, and may send tracking data to computing device 113 on the cart 120 via a wired or wireless communication link. The one or more separate computers for the motion tracking system 105 may be located on the imaging system 103, for example.

Figure 2:
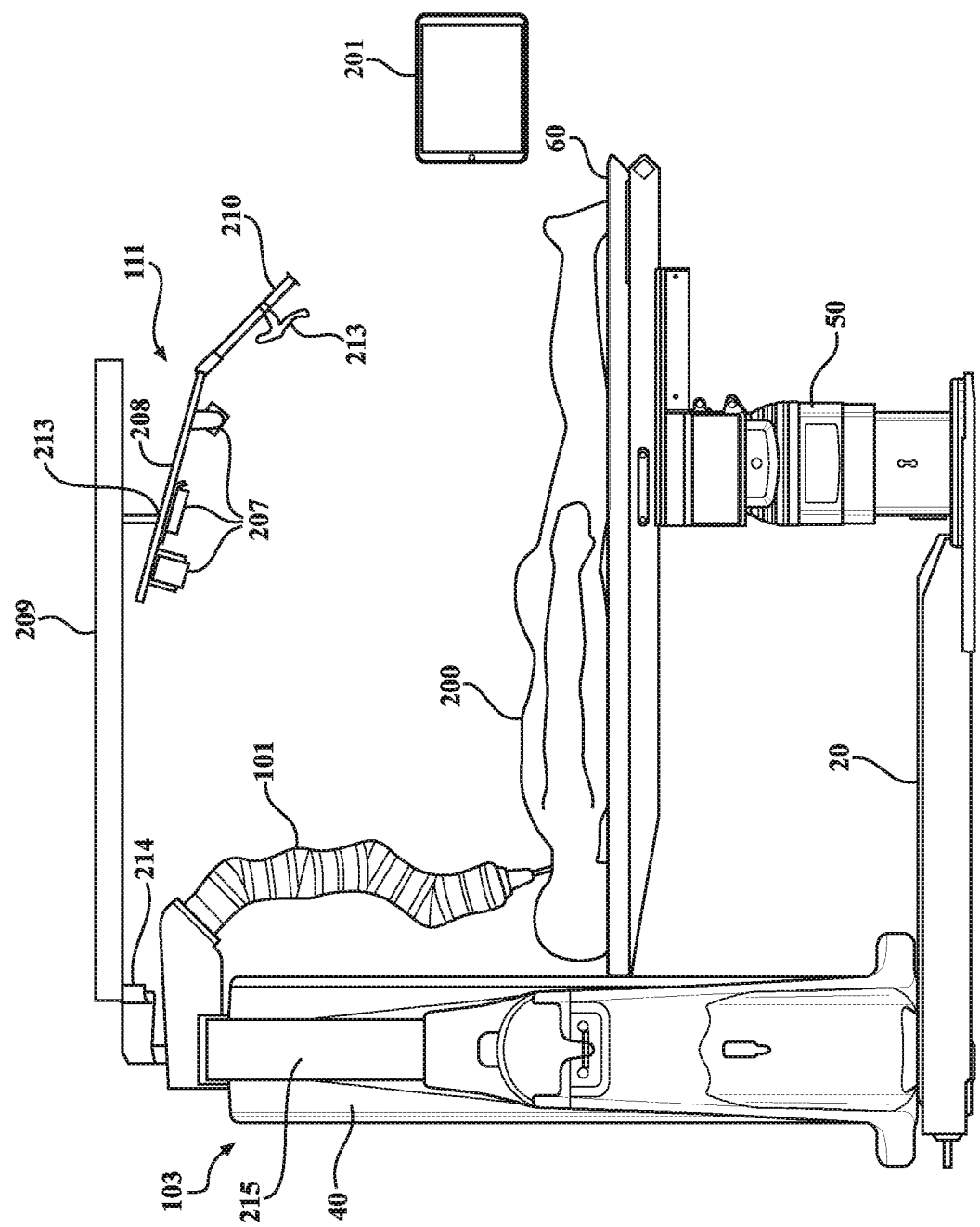
FIG. 2 shows an alternative example of a system for performing robotically-assisted image-guided surgery having an optical sensing device for a motion tracking system on an arm extending from a gantry of an imaging system.

FIG. 2 illustrates an example of a surgical system for performing robotically-assisted and image-guided surgery. In this example, the localizer 111 includes an array of cameras 207 mounted to a rigid support 208. The support 208 including the camera array 207 is suspended above the patient surgical area by an arm 209. The arm 209 may be mounted to or above the imaging device 103. The pose of the rigid support 208 may be adjustable with respect to the arm 209 to provide the camera array 207 with a clear view into the surgical field while avoiding obstructions. In some examples, the rigid support 208 may pivot with respect to the arm 209 via a joint. In some examples, the position of the rigid support 208 may be adjustable along the length of the arm 209. In some examples, the position of the rigid support 208 may be moved about the imaging device 103. A handle 210 attached to the rigid support 208 may be used to adjust the orientation and/or position of the localizer 111. The localizer 111 may be normally locked in place with respect to the arm 209 during an imaging scan or surgical procedure. A release mechanism 213 on the handle 210 may be used to unlock the localizer 111 to enable its pose to be adjusted by the user. In some examples, the arm 209 or a portion thereof may be pivotable with respect to the imaging system 103, such as via joint 214. In other examples, the arm 209 may be raised or lowered relative to the top surface of the imaging system 103. In some further examples the entire arm 209 may reciprocate (e.g., to the left or right in FIG. 2) with respect to the imaging system 103.

In some examples, the rigid support 208 and camera array 207 may be removably secured to the arm 209 so that the support 208 and cameras 207 may be detached from the system for storage and/or transport. A docking system between the arm 209 and the rigid support 208 may provide mechanical coupling between the support 208 and the arm 209 and may also provide an electrical connection for data and/or power between the arm 209 and the array of cameras 207 mounted to the support 208.

FIG. 2 also illustrates a display device that may comprise a handheld display device 401. As used herein, "handheld computing device" and "handheld display device" are used interchangeably to refer to any one or all of tablet computers, smartphones, pendant controllers, cellular telephones, personal digital assistants (PDA's), netbooks, e-readers, laptop computers, palm-top computers, wearable computers, and similar portable electronic devices or computing devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands. One or more handheld display devices 201 may be used in addition to or as an alternative to a conventional display device, such as a cart-mounted monitor display device 121 as shown in FIG. 1.

As shown in FIGS. 1 and 2, a robotic arm 101 may be fixed to the imaging device 103, such as on a support element 215 (e.g., a curved rail) that may extend concentrically over the outer surface of the O-shaped gantry 40 of the imaging device 103. In some examples, an arm 209 to which the localizer 111 is mounted may be connected to the same or a similar support element 215 (e.g., curved rail) as the robotic arm 101. The position of the robotic arm 101 and/or the support arm 209 may be adjustable along the length of the support element 215. In other examples, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. Similarly, in some nonlimiting examples, an arm 209 to which the localizer 111 is mounted may be mounted to the patient support 60 or column 50, to any of the wall, ceiling or floor in the operating room, or to a separate cart. In further examples, the robotic arm 101, the localizer 111, or both may be mounted to a separate mobile shuttle, as described in U.S. patent application Ser. No. 15/706,210, filed on Sep. 15, 2017, which is incorporated by reference herein. Although a single robotic arm 101 is shown in FIGS. 1 and 2, it will be understood that two or more robotic arms 101 may be utilized to perform a robot-assisted surgical procedure.

Various examples include systems and methods for performing image registration for computer-assisted surgery. In accordance with various examples, a patient marker device that is configured to attach to a patient includes one or more radiological (passive) markers that are identifiable in three-dimensional (3D) image data (e.g., x-ray CT and/or MRI scan data) and one or more second markers that are tracked by a motion tracking system. The second makers are herein referred to as optical markers. The optical markers may be active, passive, or both. The one or more radiological markers and the one or more optical markers of the patient tracker may have a known geometric relationship to one another. The one or more optical markers of the patient tracker may be tracked by the motion tracking system 105, and the image data may be correlated to the position of the patient at the time of the surgical intervention based on the known geometric relationship between the one or more radiological markers and the one or more of optical markers of the trackers.

Figure 3:
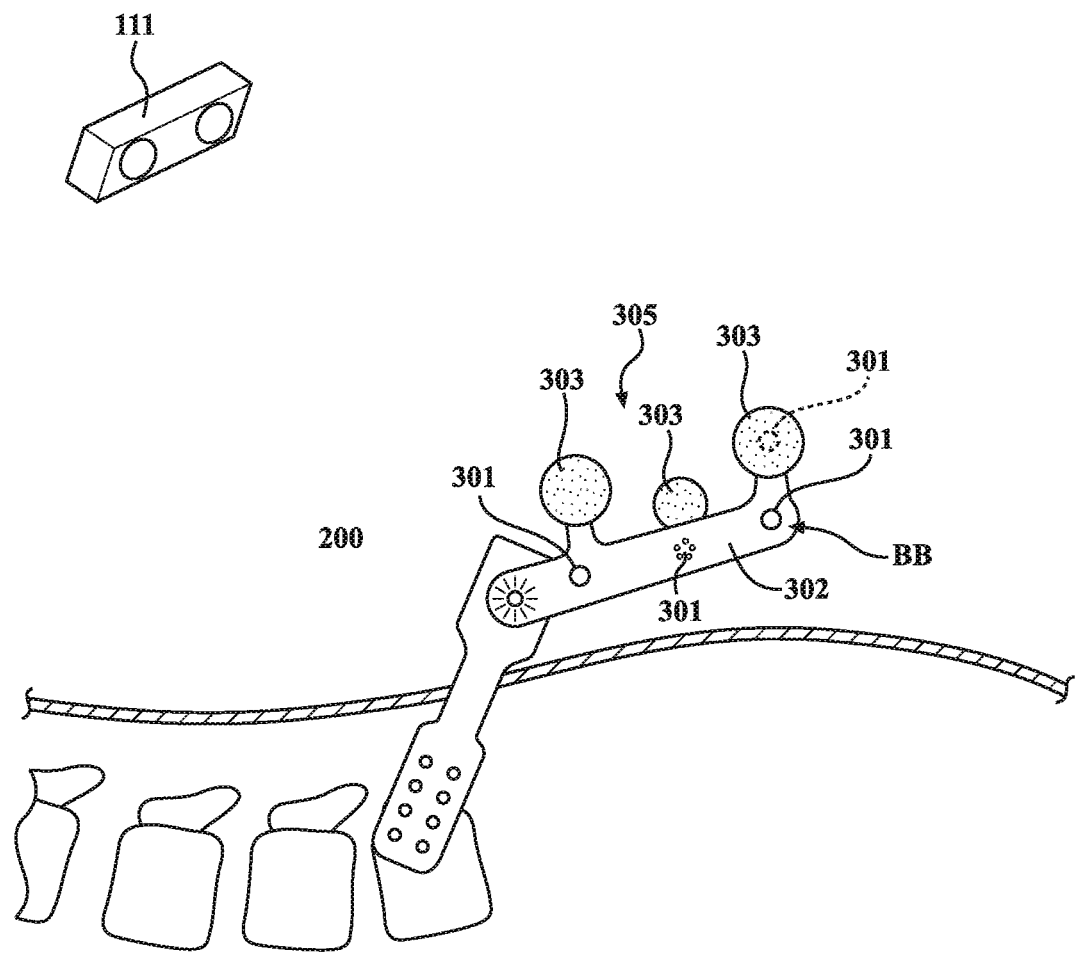
FIG. 3 illustrates a patient marker device having a plurality of radiological markers arranged in a first geometric pattern and a plurality of optical markers arranged in a second geometric pattern.

In one example of a patient tracker 305 as shown in FIG. 3, the one or more radiological markers 301 may comprise a plurality of radiological markers arranged in a first geometric pattern. As used herein, a "radiological marker" comprises a discrete element having a radiodensity that is sufficiently different from that of its surrounding environment to enable the marker to be readily identified in a radiological image (e.g., an x-ray CT reconstruction). A radiological marker may be, for example, a small bead or "BB" comprised of a radiopaque material, such as sapphire, titanium or stainless steel, that is fixed on or within the patient marker device 305. In some examples, a radiological marker may comprise a body formed of a material that is normally radiolucent, such as a thermoplastic material, that has been impregnated or "doped" with a highly-radiopaque material, such as barium. In certain examples, the patient tracker 305 may be at least partially comprised of a radiolucent material, such as plastic or carbon fiber, which may enhance the contrast between the radiological marker(s) 301 and the adjacent portion(s) of the patient tracker 305 in the radiological image.

The one or more optical markers 303 of the patient tracker 305 may comprise a plurality of optical markers arranged in a second geometric pattern. The optical markers may comprise an array of reflective elements (e.g., spheres or disks) and/or radiation emitters (e.g., LEDs) attached to the patient tracker 305 as described above with reference to FIGS. 1 and 2. The localizer 111 (e.g., a camera array 207) is positioned to detect radiation reflected by or emitted from the optical markers 303 to enable continuous real-time tracking of the patient tracker 305 in three-dimensional space. In some examples, a radiological maker 301 may be disposed within the optical marker 303. The patient tracker 305 including the one or more radiological markers 301 and the one or more optical markers 303 may be rigidly attached to the patient 200, as shown in FIG. 3.

Figure 4:
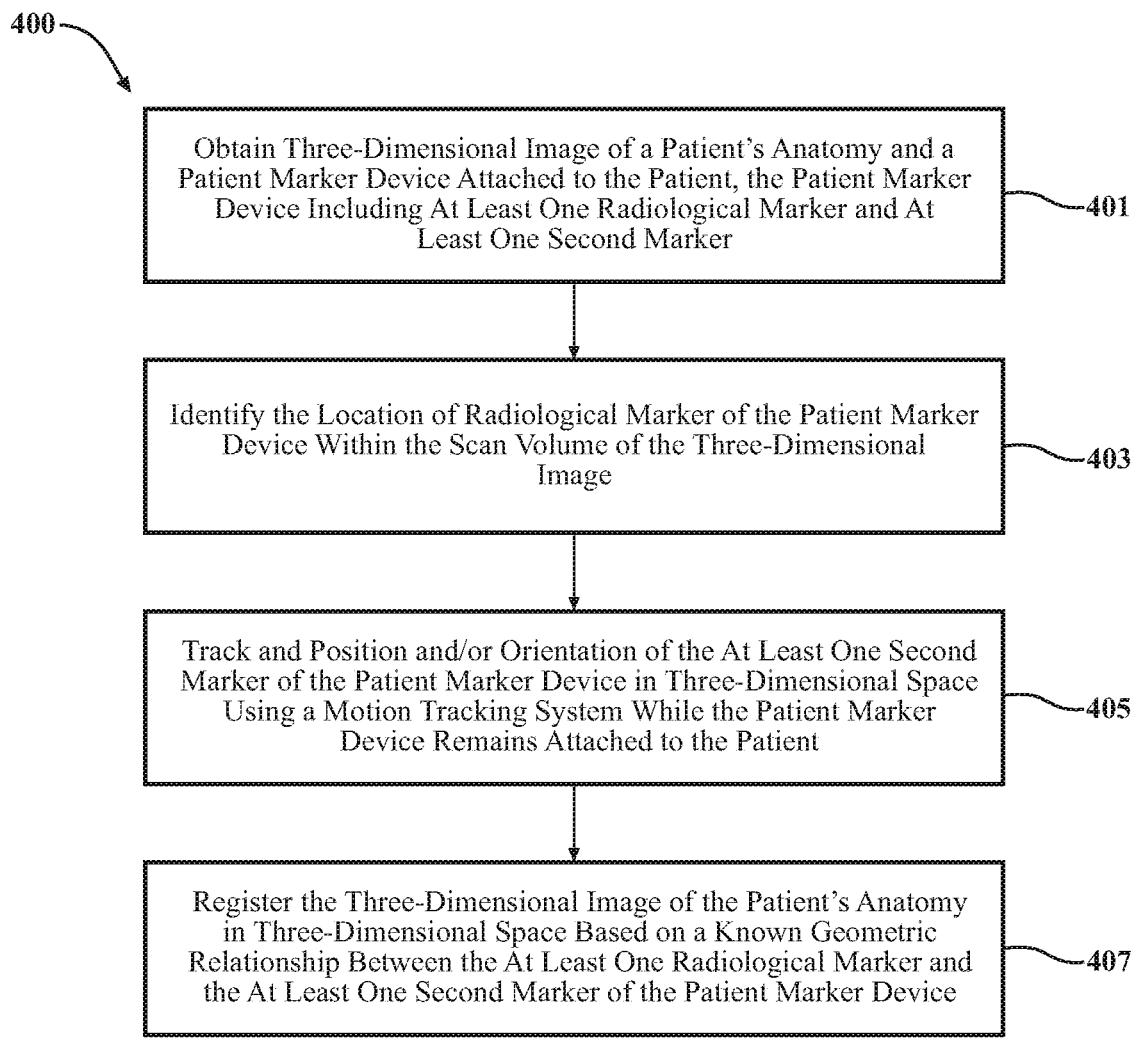
FIG. 4 is a process flow diagram illustrating a method of registering patient images using a patient tracker according to the present teachings.

FIG. 4 is a process flow diagram that illustrates a method 400 of registering patient images using a patient marker device 305 as shown in FIG. 3. Computer-assisted surgery techniques generally utilize a process of correlating a first dataset representing a portion of the patient's anatomy that is to be operated on with the position of the patient at the time of the surgical intervention. The position of the patient may be determined based on a second dataset which may include real-time camera image(s) from a motion tracking system 105 as described above. The correlation between these datasets may be accomplished computationally using software, and may be referred to as "patient image registration." The registration method 400 of FIG. 4 may be implemented using one or more computing devices or computers or controllers, such as computing device 113 shown in FIG. 1.

In block 401 of method 400, a three-dimensional image of the patient's anatomy and the one or more radiological markers 301 may be obtained using an imaging device, such as the imaging device 103 shown in FIGS. 1 and 2, while the patient marker device 305 is attached to the patient 200. In some examples, the imaging device 103, such as an x-ray CT scanning device, may perform a scan over at least a portion of the patient 200 and at least a portion of the patient marker device (patient tracker) 305 that includes the one or more radiological markers 301. During the imaging scan, the one or more second optical markers 303 may not need to be tracked or may not even need to be visible to, or within the sensing range of, the tracking sensor(s) (e.g., cameras) of the motion tracking system 105.

The scan data obtained by the imaging device 103 may be used to generate a three-dimensional reconstructed image (e.g., a tomographic reconstruction) over a scan volume. The scan volume may include at least a portion of the patient's anatomy, including the internal anatomy and/or structure(s) that are to be operated on (i.e., a surgically-relevant portion of the patient's anatomy), as well as the one or more radiological markers 301 of the patient marker device (patient tracker) 305. The scan volume may also optionally include all or a portion of the one or more second optical markers 303 of the patient tracker 305. The three-dimensional image may be stored electronically in a memory. The three-dimensional image may be in any suitable format, such as in a file format that conforms to the Digital Imaging and Communications in Medicine (DICOM) standard.

In block 403 of method 400, the location of each radiological marker 301 may be identified within the scan volume of the three-dimensional image. In various examples, segmentation software may be used to identify the locations of the radiological markers 301 within the scan volume. Identifying the locations of the radiological markers 301 may include, for example, performing a thresholding operation on the collected image dataset, or on portion(s) thereof. In the case of x-ray image data, the thresholding operation may include utilizing an algorithm to analyze the radiodensity values (e.g., Hounsfield units) associated with individual pixels/voxels in the image dataset and based on the analysis, identifying the pixels/voxels within the image data corresponding to the radiological markers 301. The radiological markers 301 may be arranged a predetermined geometric pattern, which may aid the segmentation software in finding and recognizing the radiological markers 301. Other techniques may also be utilized. The locations of the radiological markers 301 identified within the scan volume may be stored electronically in a memory, and may optionally be stored in association with the three-dimensional image data.

In block 405 of method 400, the pose of the one or more second optical markers 303 of the patient marker device (patient tracker) 305 may be tracked in three-dimensional space using the motion tracking system, such as the motion tracking system 105 shown in FIGS. 1 and 2, while the patient tracker 305 remains attached to the patient. The one or more second markers 303 may comprise optical markers (e.g., light-emitting or light-reflecting elements) that may be detected using the localizer 111 (e.g., cameras 207). The motion tracking system 105 may determine the current pose of the second markers 305 in three-dimensional space (e.g., using well-known triangulation techniques). In some examples, the second markers 303 may be tracked by the motion tracking system 105 after the patient has been scanned using the imaging device 103 (block 401), and second markers 303 need not be tracked during the imaging scan.

In block 407 of method 400, the three-dimensional image of the patient's anatomy may be registered in three-dimensional space based on the known geometric relationship between the one or more radiological markers 301 and the one or more second optical markers 303 of the patient marker device (patient tracker) 305. Because the locations of the one or more radiological markers 301 within the scan volume is known from block 403, and the locations of the one or more optical markers 303 in three-dimensional space is known from block 405, the known geometric relationship between the one or more radiological markers 301 and the one or more optical markers 303 may be used to correlate elements represented within the scan volume to their actual locations in three-dimensional space. In some examples, this may include mapping elements (e.g., voxels) of image data in the scan volume to corresponding spatial coordinates (e.g., x, y, z coordinates) in three-dimensional space. The correlation of elements represented within the scan volume of the three-dimensional image, including internal anatomical features of the patient, to the actual positions of these elements in three-dimensional space may be useful in planning and/or performing a surgical or interventional procedure. In one example, images of the patient's anatomy (e.g., 2D slices of a tomographic reconstruction and/or a 3D rendering of the patient's anatomy) may be displayed on a suitable display device, such as display 121 shown in FIG. 1. The images of the patient's anatomy may be augmented by graphical representations of other objects (e.g., surgical tools, instruments, implants, etc.) that may be tracked in "real-time" by the motion tracking system 105 in the same three-dimensional space to which the patient images are registered. Alternatively or in addition, the three-dimensional image of the patient's anatomy registered in three-dimensional space may be used to control a surgical robot, such as robotic arm 101 shown in FIG. 1. For example, the robotic arm 101 may be controlled to move the end effector 102 to a pose in three-dimensional space relative to the location of a particular anatomical feature of the patient that may be identified within the scan volume.

In examples, the known geometric relationship between the one or more radiological markers 301 and the one or more optical markers 303 may be represented as a set of data values, such as vector or transformation matrix values, and may be stored electronically in a memory. In some examples, the geometric relationship between the one or more radiological markers 301 and the one or more optical markers 303 may be unique to a particular patient tracker 305, and may be stored in association with a unique identifier for that patient marker device 305. Alternately, the geometric relationship between the one or more radiological markers 301 and the one or more optical markers 303 may be identical for a group (e.g., model) of patient trackers 305, and may be stored in association with an identifier of the group of patient trackers 305.

In accordance with certain examples, prior to use the patient tracker 305 may be pre-registered in the computing device 113 by entering identifying data for the patient tracker 305, which may be a model or serial number, for example. Alternatively, the identifying data may be obtained using an automatic identification and data capture (AIDC) technique, such as via a QR code, a bar code, an RFID tag, etc. In one example, the identifying data for the patient tracker 305 may be the geometric pattern of the second markers 303 that may be detected using the motion tracking device, where each patient tracker 305, or group(s) of patient trackers 305 sharing substantially identical characteristics, may be identified by a particular geometric pattern of the optical markers 303. The identifying data for the patient tracker 305 may include data representing the known geometric relationship between the one or more radiological markers 301 and the one or more second markers 303. Alternately the identifying data for the patient tracker 305 may be used to obtain other data representing the known geometric relationship between the one or more radiological markers 301 and the one or more second markers 303 for that patient tracker 305, such as via a lookup table or database that may be stored locally on the computing device 113 or accessed remotely over a network connection.

In examples, the patient tracker 305 may be manufactured with precise dimensions, so that the spatial relationship between the one or more radiological markers 301 and the one or more optical markers 303 may be accurately known at the time of manufacture. Alternately, the one or more radiological markers 301 may have a less precise location that is close to the position of a respective optical marker 303. In one example, the patient tracker 305 may include a rigid frame 302 with mounting posts upon which a plurality of optical markers 303 (e.g., reflective spherical elements; active LED, etc.) may be attached. Radiological markers 301 may be mounted on or within the mounting posts, the optical trackers, or both so that the geometric relationship between corresponding sets of radiological and second markers 301, 303 may be known within a very small tolerance (e.g., within 0.5 mm, such as ~0.05 mm). In some examples, the centroids of the respective radiological and second markers 301, 303 may be coincident, such that the geometric patterns defined by the radiological and optical markers 301, 303 may be identical.

Figure 5:
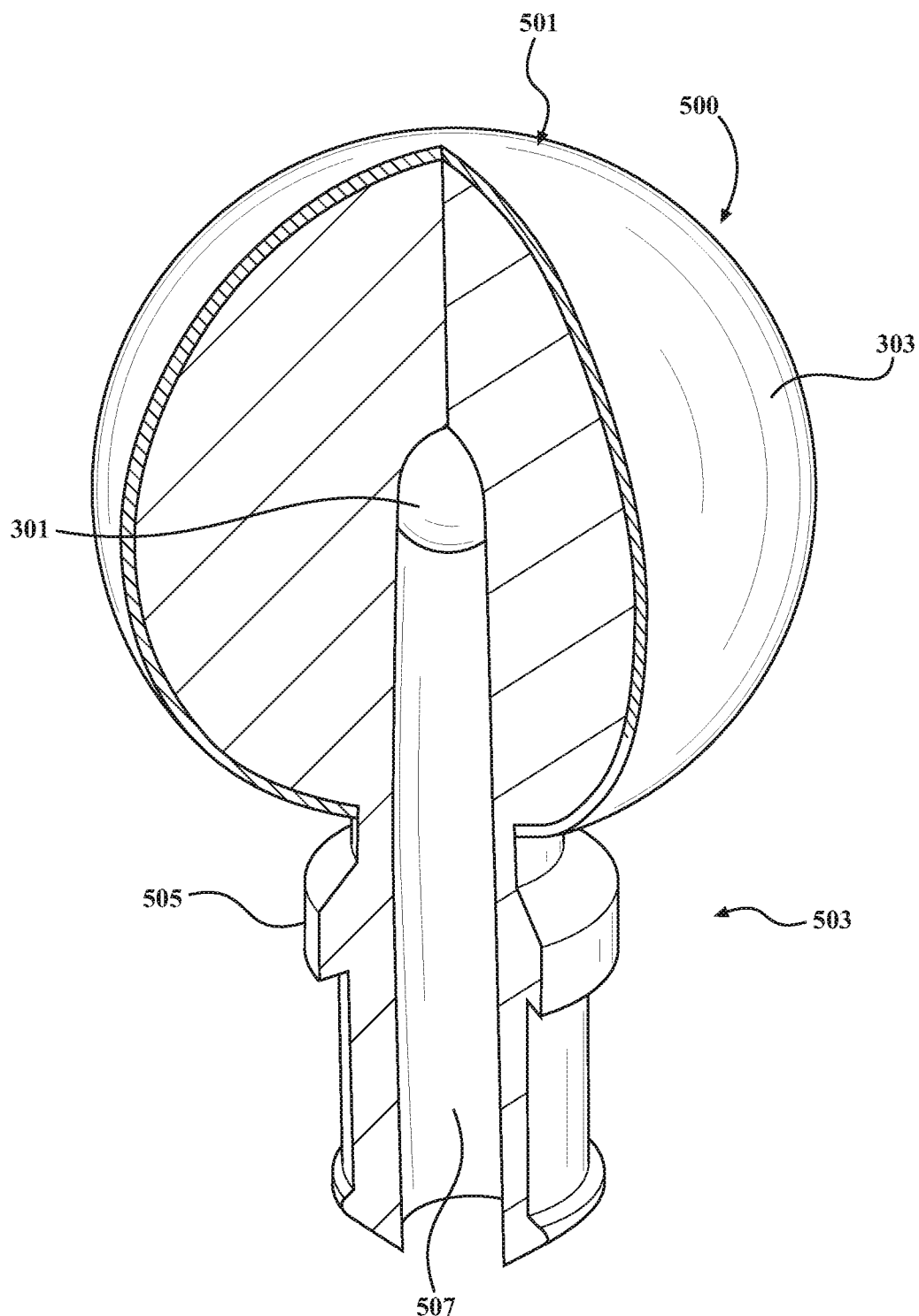
FIG. 5 illustrates a hybrid marker including a radiological marker contained within an optical marker.

FIG. 5 is a partial cut-away view of an alternative example of a "hybrid" marker 500 that includes a radiological marker 301 contained within an optical marker 303. In this example of a hybrid radiological/optical marker 500, the radiological marker 301 is located in the geometric center of a generally spherical second marker 303. The radiological marker 301 may be a small (e.g., 0.5-5 mm, such as 2 mm, diameter) bead made of radiopaque material (e.g., sapphire). The second marker 303 may be a molded component having a generally spherically-shaped upper portion 501. The spherically-shaped upper portion 501 may have a diameter between 6 mm and 20 mm, such as about 12 mm. The upper portion 501 may have a retroreflective coating over a surface of the upper portion. A lower portion 503 of the optical marker 303 may include features 505 (e.g., snap-in features) configured to facilitate attachment of the hybrid marker 500 to a patient tracker 305. Alternatively, the lower portion 503 of the hybrid marker 500 may be omitted, and the marker 500 may be attached to a patient tracker 305 by mating an internal open portion 507 of the marker 500 onto a mounting post (not shown) on the frame of a patient tracker 305. The internal open portion 507 may optionally include internal threads or other features to facilitate attachment to the mounting post.

In some examples, a patient tracker 305 as described above may include an array of hybrid radiological/optical markers 500. The position of each radiological marker 301 in the array may be nominally identical to that of the corresponding second (i.e., optical) marker 303. No coordinate transform may be necessary to determine the positions of the array radiological markers 301 relative to the array of second markers 303. In addition, errors in attaching the hybrid markers 500 to the patient tracker 305 may not have any impact on system accuracy. Hybrid markers 500 such as shown in FIG. 5 may be single-use items that are not intended or appropriate for re-sterilization and re-use. The process of attaching markers 500 to the patient tracker 305 in the operating theater may introduce a possibility for error, but even if a hybrid marker 500 as described above were incorrectly installed, this may not result in an error in perceived alignment. Similarly, damage or deflection of the rigid frame of the patient tracker 305 may not affect accuracy. In some examples, a hybrid marker 500 such as shown in FIG. 5 may be manufactured and distributed with the radiological marker 301 contained within the second (optical) marker 303, which may ensure positional accuracy and quality control. Alternatively, the radiological marker 301 and the second marker 303 may be separate components, and the first marker 301 may be placed within the second marker 303 at the time of use.

It will be understood that a patient tracker 105 may include one or more "hybrid" markers 500 as described above in addition to other types of markers. For example, a set of radiological markers 301 may include at least one radiological marker 301 that is contained within an optical marker 303, but may include additional radiological markers 301 that are not contained within an optical marker 303. In some examples, one or more additional radiological markers 301 may be located on or within a different portion of the frame 302 of the patient tracker. In some examples, one or more radiological markers 301 may be located at or adjacent to the portion of the patient tracker 105 that attaches to the patient. Similarly, a set of optical markers 303 may include a mixture of hybrid optical/radiological markers and non-hybrid optical markers (e.g., FIGS. 3 and 7).

Figure 6:
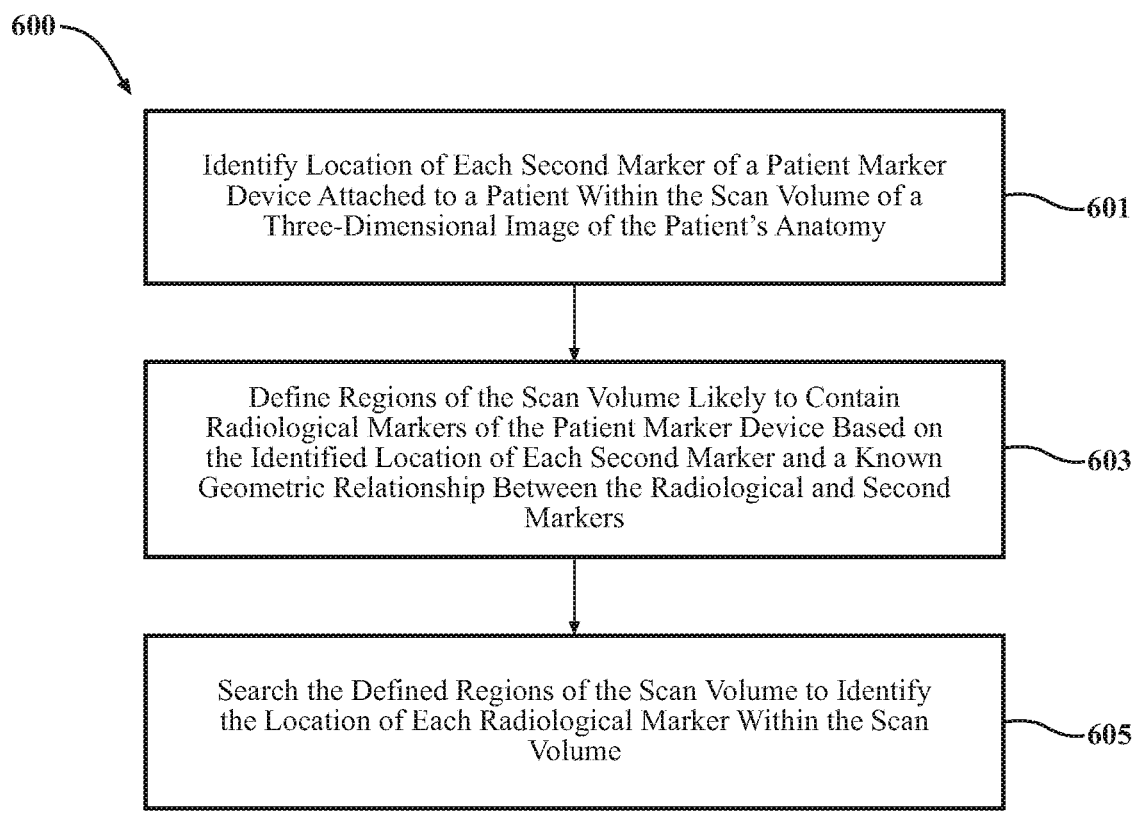
FIG. 6 is a process flow diagram illustrating a method of identifying a radiological marker within the scan volume of a three-dimensional image.

FIG. 6 is a process flow diagram that illustrates an example method 600 of identifying the location of each radiological marker 301 within the scan volume of the three-dimensional image. The method 600 may correspond to block 403 of method 400 described above with reference to FIG. 4, although it will be understood that other techniques may be used for identifying the location of each radiological marker 301 within the scan volume in accordance with method 400. In brief, the method 600 includes first identifying the location of each second (optical) marker 303, and then utilizing the identified location(s) of each second (optical) marker 303 to identify the location of each radiological marker of the set of first markers 301. As noted above, the one or more optical markers 303 may be significantly larger than the one or more radiological markers 301, and thus it may be easier to identify at least the general locations of the optical markers 303 within the scan volume than it would be to directly locate the smaller radiological markers 301 within the scan volume. Once the general locations of the optical markers 303 have been identified, the location of each radiological marker 301 may be identified based on the general location of each optical marker 303 and the known geometric relationship between the radiological markers 301 and the optical markers 303. Put another way, knowing the general location(s) of the one or more optical markers 303 may significantly narrow down the possible location(s) in which the one or more radiological markers 301 may be located.

In block 601 of method 600, the one or more optical markers 303 may be located within the scan volume of the three-dimensional image. A segmentation algorithm may be used to identify the location of each optical marker 303 within the scan volume. For example, the scan volume may be analyzed to identify one or more contiguous regions of the scan volume having radiodensity values (e.g., Hounsfield units) within a range associated with the material (s) of the one or more optical markers 303 and that have a size and shape that generally correspond to the known size and shape of the one or more optical markers 303. In some examples, the patient tracker 305 may include an array of plural optical markers 303 in a fixed geometric pattern relative to one another. This fixed geometric pattern may be previously-known, or may be accurately determined prior to or during the surgical procedure by calibrating the array of optical markers 303 of the patient tracker 305 using the motion tracking system 105. In either case, the fixed geometric pattern of the array of second optical 303 may be fed into the segmentation algorithm to assist in locating the optical set of markers 303 in the scan volume.

In block 603 of method 600, one or more regions of the scan volume that are likely to contain the one or more radiological markers 301 may be defined based on the identified location of each optical marker 303 and the known geometric relationship between the one or more radiological markers 301 and the one or more optical markers 303. By way of example, where the offset between the centroid of an optical marker 303 and the centroid of a corresponding radiological marker 301 is known to be 0.5 cm in a particular direction, then the defined region of the scan volume may be a region centered on a point that is offset by 0.5 cm in that same direction from the center of the optical marker 303 identified in block 601. The size of the defined region may be larger than the size of the radiological marker 301 to account for any inaccuracies in the localization of the optical marker 303 in block 603. In the case where one or more radiological markers 301 are co-located with a corresponding optical marker 303 (e.g., contained within a second marker 303, such as in the case of a "hybrid" marker 500 as described above), the defined region may include all of a portion of the region corresponding to the optical marker 303.

In block 605 of method 600, the one or more regions of the scan volume defined in block 603 may be searched to identify the location of each radiological marker 301 within the scan volume. Block 605 of method 600 may correspond to block 403 of method 400 as described above, and may include, for example, using segmentation software to identify the location of each radiological marker 301. As discussed above, this may include performing a thresholding operation to identify pixels/voxels within the image data corresponding to the one or more radiological markers 301. However, in accordance with block 605 of method 600, the segmentation software may only need to be utilized to analyze the region(s) of the scan volume defined in block 603, and need not be applied over the entire scan volume. This may result in a significant improvement in the efficiency of the image registration process.

Figure 7:
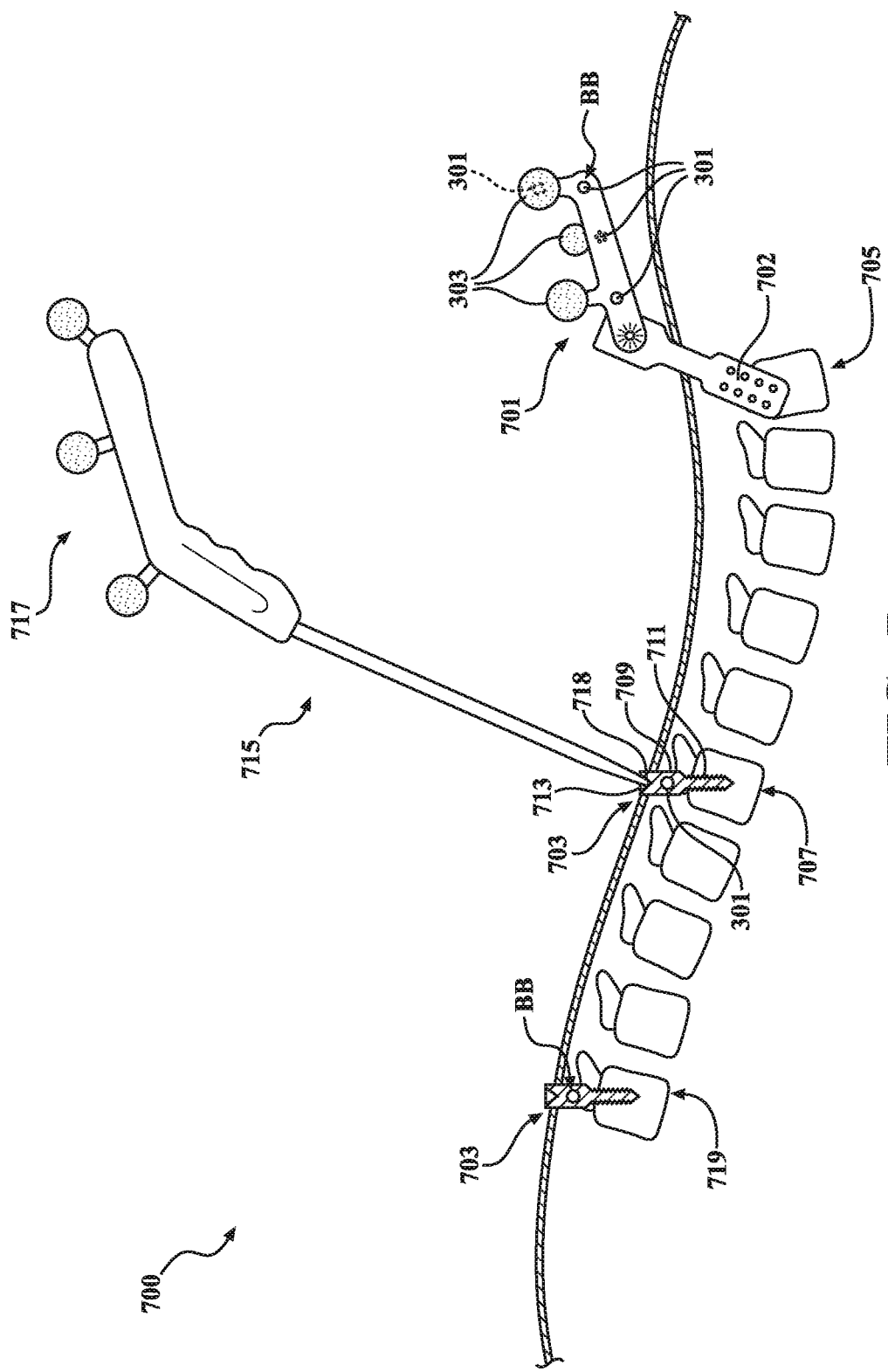
FIG. 7 illustrates a patient marker system that includes a primary patient tracker having at least one radiological marker and at least one optical marker and a plurality of secondary patient trackers having at least one radiological marker attached to different anatomic structures of a patient.

FIG. 7 illustrates an example of a patient marker system 700 that includes a primary patient tracker 701 and at least one secondary patient tracker 703. A patient marker system 700 (herein patient tracker system) as shown in FIG. 7 may be particularly useful for "complex" computer-assisted surgical procedures. As used herein, a "complex" computer-assisted surgical procedure includes a surgical intervention on multiple portions of a patient's anatomy, where the multiple portions of the patient's anatomy may move (e.g., articulate and/or shift) relative to one another by a clinically significant amount during the course of the surgical intervention. For example, a "complex spine" procedure may include a surgical intervention that spans more than two, such as three or more, vertebral levels. In such a procedure, the spine may deform to such an extent that the "virtual" three-dimensional image dataset of the patient's anatomy (e.g., a pre-operative CT scan) may no longer accurately reflect the actual patient situation.

In the patient tracker system 700 of FIG. 7, the primary patient tracker 701 may be similar or identical to the patient tracker 305 shown and described above with reference to FIG. 3, and may include one or more radiological markers 301 that may be identifiable in three-dimensional image data and one or more optical markers 303 that may be tracked by a motion tracking system. In some examples, the one or more radiological markers 301 may include an array of plural radiological markers 301 arranged in a first geometric pattern, and the one or more optical markers 303 may include an array of plural optical markers 303 arranged in a second geometric pattern. The geometric relationship between the one or more radiological markers 301 and the one or more second markers 303 may be known.

The primary patient tracker 701 may include an attachment mechanism 702, such as a clamp or threaded portion, that enables the primary patient tracker 701 to be rigidly attached to a first anatomical structure 705 of the patient. As shown in FIG. 7, the attachment mechanism 702 is a clamp that is attached to the spinous process at a first vertebral level of the spine of a patient. In other examples, the primary patient tracker 701 may be attached to a different anatomical feature, such as the iliac crest or another bony portion of the anatomy.

A secondary patient tracker 703 may be rigidly attached to a second anatomical structure 707 of the patient. In various examples, the secondary tracker 703 may include a main body 709 and an attachment mechanism 711, such as a clamp or threaded portion, that enables the secondary patient tracker 703 to be rigidly attached to the second anatomical structure 707. In the example illustrated in FIG. 7, the attachment mechanism 711 is a threaded portion that is attached to a second vertebral level of the spine of the patient.

In the example shown in FIG. 7, a main body 709 of the secondary patient tracker 703 includes a post that extends outside the surface of the patient's skin. The main body 709 may comprise a radiolucent material, such as carbon fiber or PEEK. At least one radiological marker 301, as described above with reference to FIG. 3, may be located on or within the secondary patient tracker 703, such as contained within the main body 709 of the secondary patient tracker 703. In some examples, the secondary patient tracker 703 need not include a second (i.e., optical) marker 303, although it will be understood that the secondary tracker 703 may optionally include an optical marker 303.

In examples, the secondary patient tracker 703 may be compact and have a relatively low profile above the skin surface of the patient in order to not interfere with the performance of the surgical procedure. The lack of a second (i.e., optical) marker 303 on the secondary patient tracker 703 may help to minimize interference with the surgical procedure, as many commonly-used optical markers tend to be obtrusive and prone to contamination.

FIG. 7 also illustrates a stylus 715 having a marker array 717 that enables the stylus 715 to be tracked in three-dimensional space using the motion tracking system. For example, the stylus 715 may include a set of optical markers similar to the one or more optical markers 303 of the primary patient tracker 701, arranged in a pre-determined geometric pattern to enable the motion tracking system to identify and locate the stylus 715 in three-dimensional space. The stylus 715 may be calibrated such that the geometric relationship between the marker array 717 and a tip end 718 of the stylus 715 is known. Thus, by tracking the marker array 717 using the motion tracking system 105, the location of the tip end 718 of the stylus 715 in three-dimensional space may be known, and may be displayed on a display device overlaying the patient image(s). A user may touch the tip end 718 of the stylus 715 to various landmarks on the patient and compare the actual location of the stylus 715 to the location of the stylus 715 indicated on the display device to confirm the accuracy of the image registration. In the example shown in FIG. 7, the user may touch the tip end 718 of a tracked stylus 715 to the secondary tracker 703 to confirm the accuracy of the registration.

As shown in FIG. 7, the secondary patient tracker 703 may include a touchpoint 713 on an outer surface of the secondary patient tracker 703, such as on a top surface of the secondary patient tracker 703. The touchpoint 713 may comprise a depression or opening into which the tip end 718 of a stylus 715 may be inserted. Alternately or in addition, the touchpoint 713 may be a visible target, such as a cross-hair or bullseye pattern, on a surface of the secondary tracker 703 that may be touched by the tip end 718 of the stylus 715. The touchpoint 713 may have a pre-determined geometric relationship with a radiological marker 301 of the secondary tracker 703. In some examples, a radiological marker 301 may be co-located with the touchpoint 713. Alternately, the touchpoint 703 may be offset from a radiological marker by a known distance and in a known direction.

As also illustrated in FIG. 7, the patient tracker system 700 in this example includes a primary patient tracker 701 and two secondary patient trackers 703, each attached to a different anatomical structure of the patient, which in this example are different vertebral levels 705, 707 and 719 of the patient's spine. It will be understood that the patient marker system 700 may include a single secondary patient tracker 703 attached to a different anatomical structure than the anatomical structure to which the primary patient tracker 701 is attached, or more than two secondary patient trackers 703 attached to different anatomical structures. In some examples, a patient marker system 700 may include at least one secondary patient tracker 703 and more than one primary patient trackers 701 attached to different anatomical structures of the patient.

Figure 8:
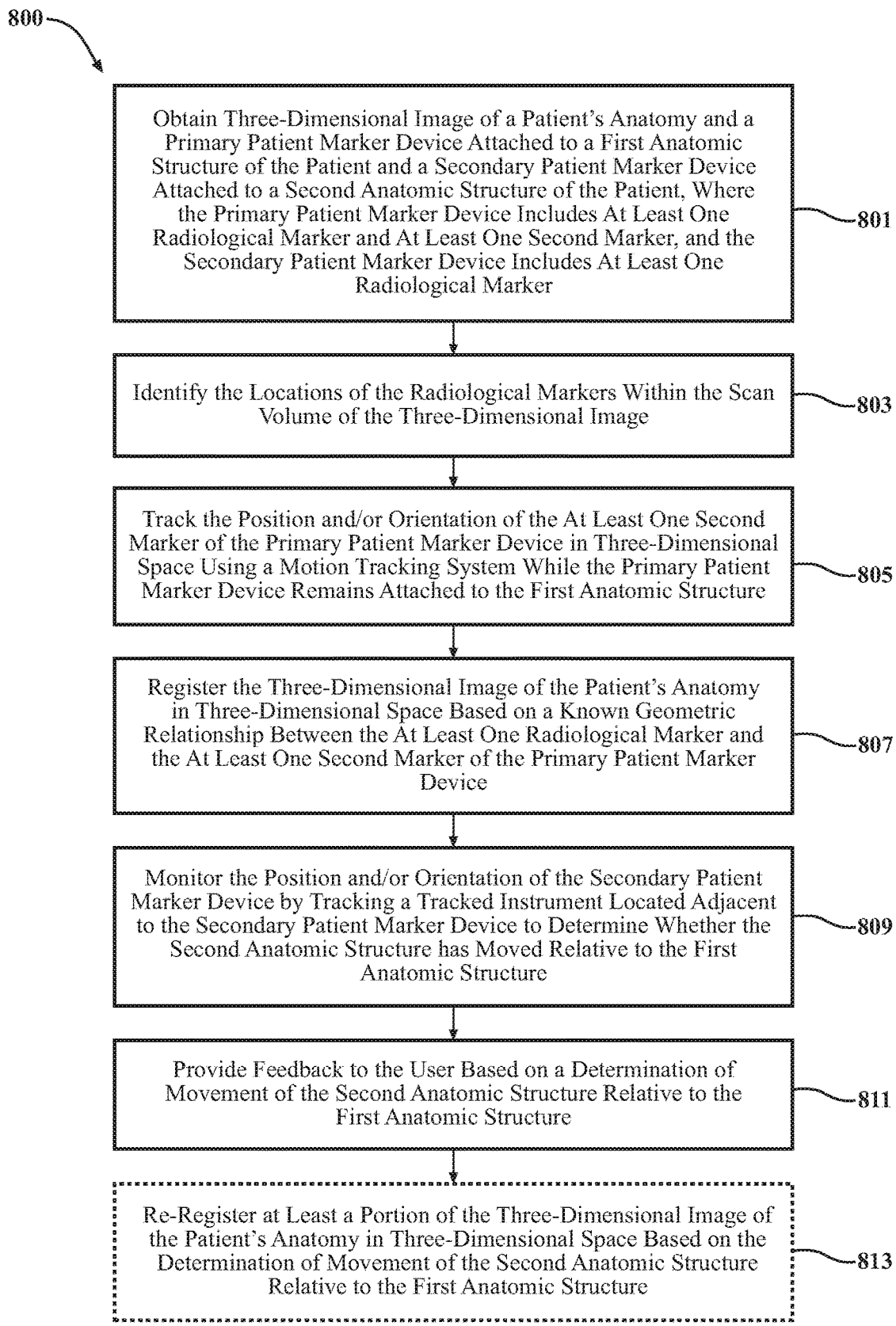
FIG. 8 is a process flow diagram illustrating a method of registering patient images using a patient tracker system as shown in FIG. 7.

FIG. 8 is a process flow diagram that illustrates an example method 800 of registering patient images using a patient marker system 700 as shown in FIG. 7. In block 801 of method 800, a three-dimensional image of the patient's anatomy may be obtained, where the three-dimensional image includes a patient marker system 700 having a primary patient tracker 701 attached to a first anatomic structure 705 of the patient and a secondary patient tracker 703 attached to a second anatomic structure 707 of the patient. In some examples, the three-dimensional image may include a plurality of secondary patient trackers 703 each attached to a different anatomic structure 707, 719, such as shown in FIG. 7. In the case of a complex surgical procedure on a patient's spine, for example, the primary patient tracker 701 may be attached to a first vertebral level 705, and a plurality of secondary patient trackers 703 may each be attached to different vertebral levels 707, 719 of the patient's spine. The primary patient tracker 701 includes at least one radiological marker 301 and at least one optical marker 303, as described above with reference to FIG. 7. The secondary patient tracker(s) 703 each include at least one radiological marker 301.

In block 803 of method 800, the locations of the radiological markers 301 of the patient maker system 700 may be identified within the scan volume of the three-dimensional image. A segmentation algorithm may be used to identify the locations of the radiological markers 301, as described above. The algorithm may be further configured to identify whether each radiological marker 301 is located on the primary patient tracker 701 or on a respective secondary patient tracker 703 (e.g., based on a known pattern of radiological markers 301, the size and shape of the marker 301, the distance(s) between the marker 301 and neighboring markers, etc.). The locations of the radiological markers 301 on the primary patient tracker 701 and on each secondary patient tracker 703 may be stored electronically in a memory, and may optionally be stored in association with the three-dimensional image data.

The locations of the radiological markers 301 within the scan volume may be used to indicate the relative positions of the anatomic structures 705, 707, 719 to which the respective markers 301 are attached. In one example, the identified location(s) of the one or more radiological markers 301 on the primary patient tracker 701 may be used to define a "benchmark" position of the first anatomic structure 705. The benchmark position may be co-located with a radiological marker 301 on the primary patient tracker 701. Alternately, the benchmark position may have a pre-defined offset from a radiological marker 301. Where the primary patient reference tracker 701 includes a plurality of radiological markers 301, the benchmark position may be defined with respect to the plurality of radiological markers 301, such as at the centroid of the plurality of radiological markers 301.

Similarly, the location(s) of the one or more radiological markers 301 on each secondary patient tracker 703 may be used to define the position of a respective anatomic structure 707, 719 with respect to the "benchmark" position. In one example, the identified location(s) of the one or more first markers 301 on each secondary patient tracker 703 may be used to define a series of "spline points," where each spline point is fixed relative to a different anatomic structure 707, 719. The position of each spline point may be defined to be co-located with a radiological marker 301, or may be defined to have a pre-determined offset from a radiological marker 301. In the example of FIG. 7, for example, the position of each spline point may be defined to be coincident with the touchpoint 713 on the secondary patient tracker 703.

In block 805 of method 800, the pose of one or more optical markers 303 of the primary patient tracker 701 may be tracked in three-dimensional space using the motion tracking system while the primary patient tracker 701 remains attached to the patient. In block 807, the three-dimensional image of the patient's anatomy may be registered in three-dimensional space based on a known geometric relationship between the one or more radiological markers 301 and the one or more optical markers 303 of the primary patient tracker 701. In some examples, the locations of the "benchmark" position of the first anatomic structure 705 and one or more "spline" points corresponding to other anatomic structures 707, 719 may also be registered in three-dimensional space. In some examples, a baseline spline curve may be generated with the benchmark and spline points being the control points for the baseline spline curve.

In block 809 of method 800, the pose of a secondary patient tracker 703 may be monitored using the motion tracking system to determine whether there has been movement of the second anatomic structure 707 relative to the first anatomic structure 705. In some examples, the pose of the secondary patient tracker 703 may be monitored when an operator places a tracked instrument, such as a stylus 717 as described above with reference to FIG. 7, adjacent to the secondary patient tracker 703. In one non-limiting example, the operator may bring the tip end 718 of the stylus 717 into contact with a touchpoint 713 on the secondary patient tracker 703. The current location of the touchpoint 713 in three-dimensional space relative to the benchmark position of the first anatomic structure 705 may be compared to the location of the touchpoint 713 relative to the benchmark position at the time of image registration in block 807. Any movement of the touchpoint 713 relative to the benchmark position may be determined and optionally quantified in terms of its magnitude and direction.

This process may be repeated for each secondary patient tracker 703 of the patient marker system 700 that is attached to a different anatomic structure 707, 719 to determine whether the respective anatomic structure 707, 719 has moved relative to the first anatomic structure 705. In some examples, the user may be prompted to monitor the position of the secondary patient tracker(s) 703 at various times during a surgical procedure, such as via a visual message or image on a display device 121 and/or an audio message or alert.

In block 811 of method 800, feedback may be provided to the user based on a determination of movement of the second anatomic structure 707 relative to the first anatomic structure 705. For example, a perceptible warning (e.g., a visual warning on a display 121, an audio message or alert, or a haptic alert), may be provided to the user when the second anatomic structure 707 has moved relative to the first anatomic structure 705 by more than a threshold amount. Alternatively or in addition, a visual indicator of the magnitude and/or direction of the movement of the second anatomic structure 707 relative to the first anatomic structure 705 may be provided on a display device 121. This may aid the surgeon in compensating for relative movement of the patient's anatomy. For example, in a multi-level spine procedure, if a secondary patient tracker 703 attached to a particular vertebral level has shifted by a given amount in one direction relative to the benchmark, it may be inferred that the vertebral level midway between the benchmark and that vertebral level has shifted by approximately half that amount in the same direction.

In optional block 813, at least a portion of the three-dimensional images of the patient's anatomy may be re-registered in three-dimensional space based on the detected movement of the second anatomic structure 707 with respect to the first anatomic structure 705. For example, where it is determined that the second anatomic structure 707 has moved relative to the first anatomic structure 705 by a particular amount in a particular direction, portions of the image data (e.g., voxels) corresponding to the second anatomic structure 707 may be re-registered in three-dimensional space to compensate for the detected movement. Other portions of the image data corresponding to different anatomic structures 719 having a secondary patient tracker 703 attached may be similarly re-registered in three-dimensional space to compensate for the detected movement of the anatomic structure 719 relative to the first anatomic structure 705. Intervening portions of image data (i.e., between anatomic structures to which the primary and secondary patient trackers 701, 703 are attached) may optionally be re-reregistered based on an interpolation of the movement of the corresponding anatomy relative to the first anatomic structure 705.

In examples where a baseline spline curve is generated using the locations of the "benchmark" position and one or more "spline" points as control points, as described above, an updated spline curve may be generated with the "benchmark" position and the updated locations of the "spline" points as the control points for the updated spline curve. Portions of the image data (e.g., voxels, axial slices, etc.) may be re-registered in three-dimensional space based on the change in the spline curve between the baseline curve and the updated curve.

Figure 9:
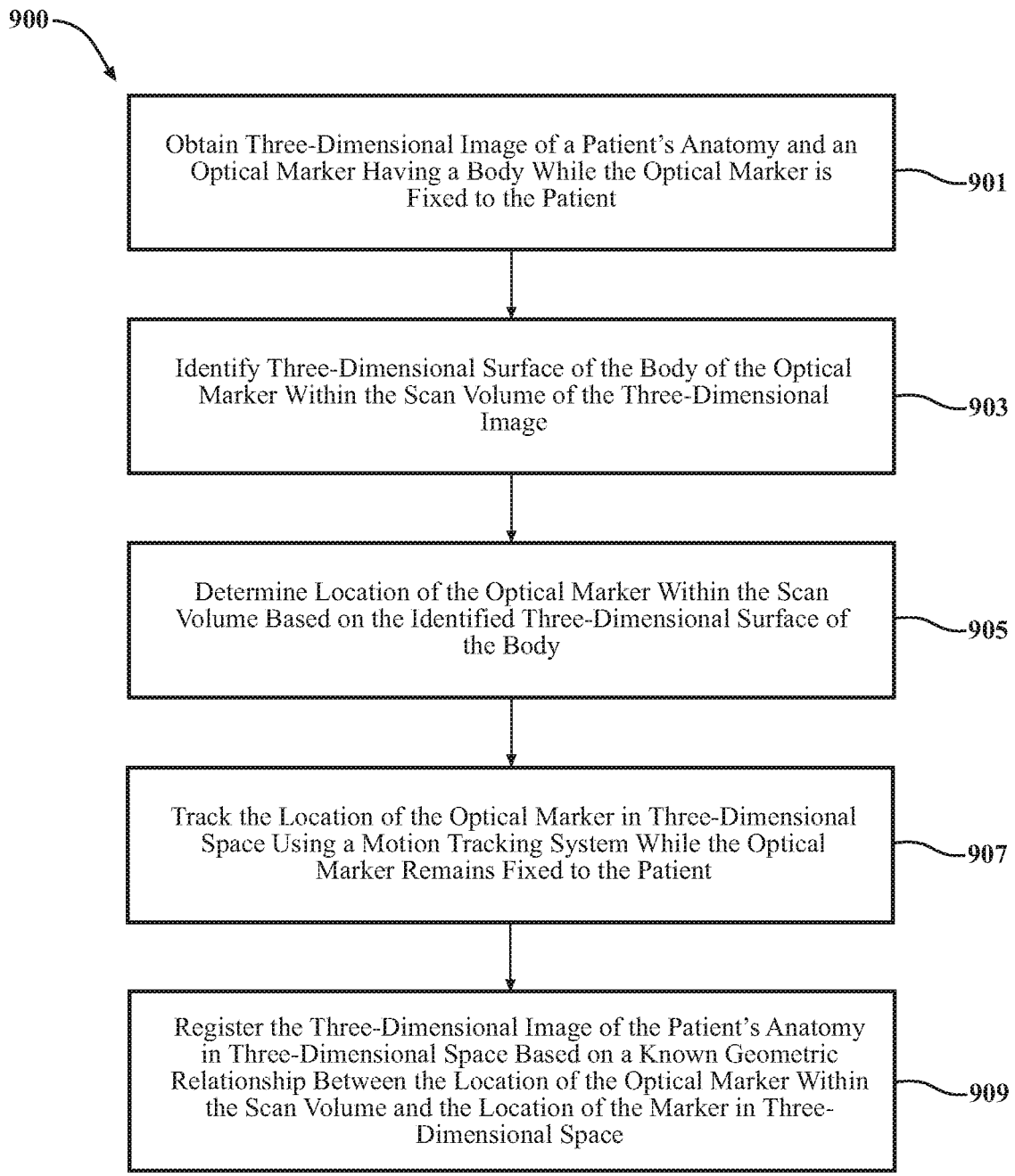
FIG. 9 is a process flow diagram illustrating a method of registering patient images using a patient tracker that includes at least one optical marker having a body that is comprised of a radiopaque material.

FIG. 9 is a process flow diagram that illustrates yet another example method 900 of registering patient images for computer-assisted surgery. Method 900 may be used for image registration in conjunction with a patient tracker 305 that includes at least one optical marker having a body. In some examples, the body may be comprised of a thermoplastic material that may be impregnated or "doped" with a highly radiopaque material, such as barium, bismuth subcarbonate, barium sulfate, bismuth oxychloride, bismuth trioxide, tungsten and tantalum. Examples of a passive optical marker having a body comprised of a radiopaque material are described in U.S. Pat. No. 8,662,684 to Shafer et al. (assigned to IZI Medical Products), the entire teachings of which are incorporated herein by reference. The body of the optical marker may be formed using a molding process, such as injection molding. In other examples, where there is sufficient radiodensity contrast between the body of the optical marker and its surrounding environment (e.g., air), the body may not need to be doped with radiopaque material. The body of the optical marker may have a spherically-shaped upper portion and a lower portion that facilitates attachment to the patient tracker 305. The spherically-shaped upper portion may have a diameter between 6 mm and 20 mm, such between 8 mm and 16 mm, including about 12 mm. The optical marker may be a passive marker, and may include an optically reflective layer (e.g., a retroreflective coating) on a surface of the body.

Alternately, in some examples, the optical marker may be an active marker that includes a light emitting source (e.g., an LED) and a body. In some nonlimiting examples, the body may optionally be comprised of a radiopaque material, such as a thermoplastic material doped with a highly-radiopaque substance, as described above. Light from the light emitting source may pass through the body of the marker and out from the outer surface of the body. In some examples, the body of the marker may be radiodense to x-rays but transparent to light in the visible and/or infrared spectrum. An optical diffuser layer may be formed on or provided over a surface of the body to diffuse the light as is transmitted from the marker.

In block 901 of method 900, a three-dimensional image of a patient's anatomy and an optical marker having a body may be obtained while the optical marker is fixed to the patient. The three-dimensional image may include an array of plural optical markers on a patient tracker 305. The patient tracker 305 may be attached to a bony portion of the patient's anatomy, as discussed above.

Figure 10:
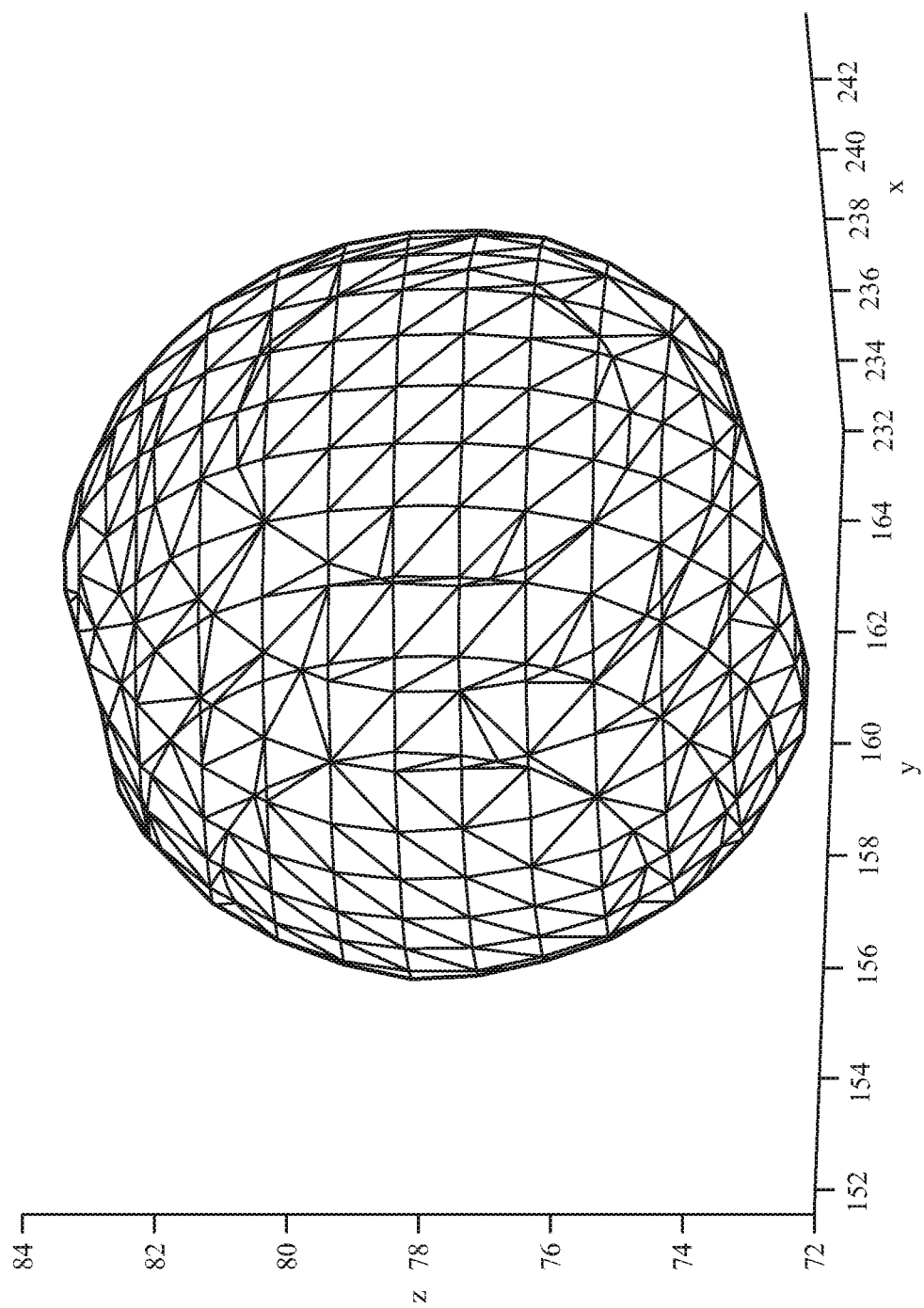
FIG. 10 is a three-dimensional plot of a surface of a body for an optical marker that has been doped with radiopaque material that was identified in a CT scan using image segmentation.

In block 903 of method 900, a three-dimensional surface of the body of the optical marker may be identified within the scan volume of the three-dimensional image. A segmentation algorithm may find the three-dimensional surface of the body in the image data with sufficient accuracy and precision based on the contrast in radiodensity between the body of the optical marker and its surroundings. FIG. 10 illustrates a three-dimensional plot of a surface of an optical marker body that has been doped with radiopaque material that was identified in a CT scan using image segmentation.

In block 905 of method 900, the location of the optical marker within the scan volume may be determined based on the identified three-dimensional surface of the body of the marker. In some examples, the location of the optical marker may correspond to the centroid of the three-dimensional surface of the body, which may nominally be considered equivalent to the centroid of the optical marker as detected by the motion tracking system. Thus, no coordinate transformation is needed between the location of the marker within the scan volume and in three-dimensional space.

In block 907 of method 900, the location of the optical marker may be tracked in three-dimensional space using the motion tracking system while the optical marker remains fixed to the patient. In block 909 of method 900, the three-dimensional image of the patient's anatomy may be registered in three-dimensional space based on a known geometric relationship between the location of the optical marker in the scan volume and the location of the marker in three-dimensional space. As discussed above, In some examples where the location of the marker within the scan volume is the centroid of the three-dimensional surface of the body of the marker, the location of the marker in the scan volume is co-located with the location of the marker in three-dimensional space, so that no coordinate translation needs to be performed.

Figure 11:
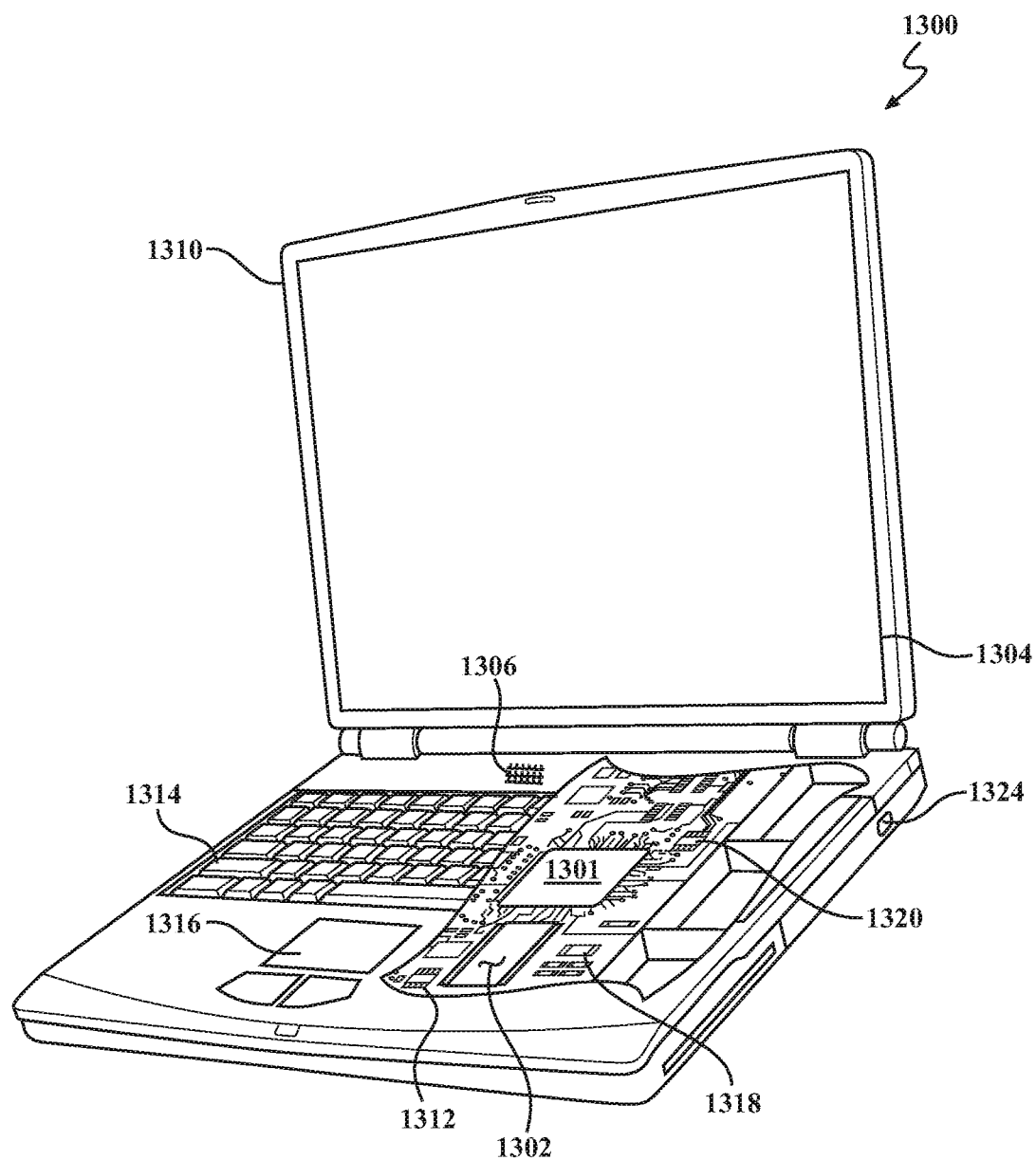
FIG. 11 schematically illustrates a computing device.

FIG. 11 schematically illustrates a computing device 1300 useful for performing and implementing the various examples described above. In some examples, the computing device 1300 may be the same or similar to computing device 113 and hand-held computer 201 illustrated in FIGS. 1 and 2. The computing device 1300 may perform the functions of an image guided surgery system, a robotic surgery system, a computer-assisted surgery system, or a combination thereof. In some examples, one or more computing devices 1300 may be used. In one non limiting example, computing device 1300 may be a robot controller. While the computing device 1300 is illustrated as a laptop computer in one example shown in FIG. 11, a computing device providing the functional capabilities of the computing device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). In some examples, a laptop computer, desktop computer, hand-held computer 1300 may also include a user input device such as a touch screen, a keyboard 1314, a mouse/trackpad 1316 for receiving user inputs.

The foregoing description is merely illustrative in nature and is in no way intended to limit the disclosure, its application, or uses. The broad teachings of the disclosure can be implemented in a variety of forms. Therefore, while this disclosure includes particular configurations, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the configurations is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In this application, including the definitions below, the term "controller 90" may be replaced with the term "circuit." The term "controller 90" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The computing device 1300 may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WWI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The computing device 1300 may communicate with other controllers using the interface circuit(s). Although the computing device 1300 may be depicted in the present disclosure as logically communicating directly with other controllers, in various implementations the computing device 1300 may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the computing device 1300 may be distributed among multiple controllers that are connected via the communications system. For example, multiple controllers may implement the same functionality distributed by a load balancing system. In a further example, the functionality of the controller 90 may be split between a server (also known as remote, or cloud) controller and a client (or, user) controller.

Some or all hardware features of the computing device 1300 may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SSENSORLINK, and Python®.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

The present disclosure also comprises the following clauses, with specific features laid out in dependent clauses, that may specifically be implemented as described in greater detail with reference to the configurations and drawings above.

CLAUSES

I. A method of registering patient images in a computer-assisted surgery system, comprising:
  obtaining a three-dimensional image of a patient's anatomy and an optical marker having a body while the optical marker is fixed to the patient;
  identifying a three-dimensional surface of the body of the optical marker within a scan volume of the three-dimensional image;
  determining a location of the optical marker within the scan volume based on the identified three-dimensional surface of the body;
  tracking the location of the optical marker in three-dimensional space using a motion tracking system while the optical marker remains fixed to the patient; and
  registering the three-dimensional image of the patient's anatomy in three-dimensional space based on a known geometric relationship between the location of the optical marker within the scan volume and the location of the optical marker in three-dimensional space.

II. The method of clause I, wherein determining the location of the optical marker within the scan volume based on the identified three-dimensional surface of the body comprises finding a centroid of the three-dimensional surface of the body.

III. The method of any one of the preceding clauses, wherein the body of the optical marker is comprised of radiopaque material.

IV. The method of any one of clauses I or III, wherein the body of the optical marker comprises a thermoplastic material that is doped with radiopaque material.

V. The method of any one of clauses III or IV, wherein the radiopaque material comprises at least one of barium, bismuth subcarbonate, barium sulfate, bismuth oxychloride, bismuth trioxide, tungsten and tantalum.

VI. The method of any one of the preceding clauses, wherein the body of the optical marker comprises a spherically-shaped portion having an optically reflective layer on the body.

VII. The method of any one of the preceding clauses, wherein the optical marker comprises a light emitting source.

VIII. The method of any one of the preceding clauses, further comprising performing a scan of the patient using an imaging device while the optical marker is fixed to the patient.

IX. A computer-assisted surgery system, comprising:
  an optical marker having a body;
  a motion tracking system for tracking a location of the optical marker; and
  a computing device being configured to:
    obtain a three-dimensional image of a patient's anatomy and the optical marker while the optical marker is fixed to the patient;
    identify a three-dimensional surface of the body of the optical marker within a scan volume of the three-dimensional image;
    determine a location of the optical marker within the scan volume based on the identified three-dimensional surface of the body;
    track the location of the optical marker in three-dimensional space using the motion tracking system while the optical marker remains fixed to the patient; and
    register the three-dimensional image of the patient's anatomy in three-dimensional space based on a known geometric relationship between the location of the optical marker within the scan volume and the location of the optical marker in three-dimensional space.

X. The computer-assisted surgery system of clause IX, wherein determining the location of the optical marker within the scan volume based on the identified three-dimensional surface of the body comprises finding a centroid of the three-dimensional surface of the body.

XI. The computer-assisted surgery system of any one of clauses IX or X, wherein the body of the optical marker is comprised of radiopaque material.

XII. The computer-assisted surgery system of any one of clauses IX or XI, wherein the body of the optical marker comprises a thermoplastic material that is doped with radiopaque material.

XIII. The computer-assisted surgery system of any one of clauses XI or XII, wherein the radiopaque material comprises at least one of barium, bismuth subcarbonate, barium sulfate, bismuth oxychloride, bismuth trioxide, tungsten and tantalum.

XIV. The computer-assisted surgery system of any one of clauses IX-XIII, wherein the body of the optical marker comprises a spherically-shaped portion having an optically reflective layer on the body.

XV. The computer-assisted surgery system of any one of clauses IX-XIV, wherein the optical marker comprises a light emitting source.

XVI. The computer-assisted surgery system of any one of clauses IX-XV, further comprising an imaging device configured to perform a scan of the patient while the optical marker is fixed to the patient.

XVII. A method of registering patient images in a computer-assisted surgery system, comprising:
  obtaining a three-dimensional image of a patient's anatomy and a patient tracker attached to the patient, the patient tracker including at least one radiological marker and at least one second marker;

identifying a location of the at least one radiological marker of the patient tracker within a scan volume of the three-dimensional image;

tracking a pose of the at least one second marker of the patient tracker in three-dimensional space using a motion tracking system while the patient tracker remains attached to the patient; and registering the three-dimensional image of the patient's anatomy in three-dimensional space based on a known geometric relationship between the at least one radiological marker and the at least one second marker of the patient tracker.

XVIII. The method of clause XVII, wherein the at least one second marker comprises at least one optical marker.

XIX. The method of any one of clauses XVII or XVIII, wherein obtaining a three-dimensional image of a patient's anatomy comprises performing a scan of the patient using an imaging device.

XX. The method of clause XIX, wherein during the scan of the patient, the at least one second marker does not need to be tracked by the motion tracking device to register the three-dimensional image.

XXI. The method of any one of clauses XVII-XX, further comprising:

displaying the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

XXII. The method of any one of clauses XVII-XXI, further comprising:

controlling a surgical robot to move an end effector of the surgical robot to a pose in three-dimensional space relative to a location of an anatomical feature of the patient that is identified within the scan volume of the three-dimensional image of the patient's anatomy.

XXIII. The method of any one of clauses XVII-XXII, further comprising:

storing data representing the known geometric relationship between the at least one radiological marker and the at least one second marker of the patient tracker in a memory of the computer-assisted surgery system.

XXIV. The method of clause XVII, wherein data representing the known geometric relationship is stored in memory of the computer-assisted surgery system during a registration process that includes at least one of:

providing identifying data for the patient tracker to the computer-assisted surgery system; and determining a geometric pattern of a plurality of second markers of the patient tracker using the motion tracking system.

XXV. The method of any one of clauses XVII-XXIV, wherein the at least one radiological marker comprises a discrete element comprised of radiopaque material having at least one dimension between 0.5 and 5 mm.

XXVI. The method of any one of clauses XVII-XXV, wherein the patient tracker comprises at least one hybrid marker having a radiological marker contained within a second marker.

XXVII. The method of clause XXVI, wherein the second marker comprises an optical marker having a spherically-shaped portion with a reflective coating over the spherically-shaped portion.

XXVIII. The method of any one of clauses XXVI or XXVII, wherein the radiological marker is located at a centroid of the spherically-shaped portion of the second marker.

XXIX. The method of any one of clauses XVII-XXVIII, wherein identifying the location of the at least one radiological marker of the patient tracker within the scan volume of the three-dimensional image comprises:

identifying a location of each second marker of the patient tracker within the scan volume of the three-dimensional image of the patient's anatomy;

defining one or more regions of the scan volume that are likely to contain a radiological marker based on the identified location of each second marker within the scan volume of the three-dimensional image of the patient's anatomy; and searching the one or more defined regions of the scan volume to identify a location of each radiological marker within the scan volume.

XXX. A computer-assisted surgery system, comprising:

a patient tracker comprising at least one radiological marker and at least one second marker and configured to attach to a patient;

a motion tracking system; and a computing device being configured to:

obtain a three-dimensional image of a patient's anatomy and the patient tracker;

identify a location of the at least one radiological marker of the patient tracker within a scan volume of the three-dimensional image;

track a pose of the at least one second marker of the patient tracker in three-dimensional space using the motion tracking system while the patient tracker remains attached to the patient; and register the three-dimensional image of the patient's anatomy in three-dimensional space based on a known geometric relationship between the at least one radiological marker and the at least one second marker of the patient tracker.

XXXI. The computer-assisted surgery system of clause XXX, further comprising:

an imaging device configured to perform a scan of the patient while the patient tracker is attached to the patient.

XXXII. The computer-assisted surgery system of any one of clauses XXX or XXXI, further comprising:

a surgical robot having a controller that is configured to move an end effector of the surgical robot to a pose in three-dimensional space relative to the location of an anatomical feature of the patient that is identified within the scan volume of the three-dimensional image of the patient's anatomy.

XXXIII. A method of registering patient images in a computer-assisted surgery system, comprising:

obtaining a three-dimensional image of a patient's anatomy and a primary patient tracker attached to a first anatomic structure of the patient and a secondary patient tracker attached to a second anatomic structure of the patient, the primary patient tracker including at least one radiological marker and at least one second marker, and the secondary patient tracker including at least one radiological marker;

identifying locations of the radiological markers within a scan volume of the three-dimensional image;

tracking a pose of the at least one second marker of the primary patient tracker in three-dimensional space using a motion tracking system while the primary patient tracker remains attached to the first anatomic structure;

registering the three-dimensional image of the patient's anatomy in three-dimensional space based on a known geometric relationship between the at least one radiological marker and the at least one second marker of the primary patient tracker;

monitoring the pose of the secondary patient tracker by tracking a tracked instrument located adjacent to the secondary patient tracker in three-dimensional space using the motion tracking system to determine whether the second anatomic structure has moved relative to the first anatomic structure; and providing feedback to a user of the computer-assisted surgery system based on a determination of movement of the second anatomic structure relative to the first anatomic structure.

XXXIV. The method of clause XXXIII, further comprising:

re-registering at least a portion of the three-dimensional image of the patient's anatomy in three-dimensional space based on the determination of movement of the second anatomic structure relative to the first anatomic structure.

XXXV. The method of any one of clauses XXXIII or XXXIV, wherein the three-dimensional image includes a plurality of secondary patient trackers attached to different anatomic structures of the patient, each secondary patient tracker including at least one radiological marker.

XXXVI. The method of clause XXXV, further comprising:

defining a benchmark position based on the identified location of the at least one radiological marker of the primary patient tracker within the scan volume and a plurality of spline points based on the identified locations of the radiological markers of the secondary patient trackers within the scan volume;

generating a benchmark spline curve with the benchmark position and the plurality of spline points as control points for a spline curve;

generating an updated spline curve based on a change in position of one or more spline points relative to the benchmark position detected using the motion tracking system; and re-registering at least a portion of the three-dimensional image of the patient's anatomy in three-dimensional space based on a change in the spline curve between the benchmark spline curve and the updated spline curve.

XXXVII. The method of any one of clauses XXXIII-XXXVI, wherein the pose of the secondary patient tracker is monitored while the tracked instrument contacts a touchpoint on a surface of the secondary patient tracker.

XXXVIII. The method of any one of clauses XXXIII-XXXVII, wherein the movement of the second anatomic structure relative to the first anatomic structure is determined based on a known geometric relationship between the touchpoint and the at least one radiological marker of the secondary patient tracker.

XXXIX. The method of any one of clauses XXXIII-XXXVIII, wherein the tracked instrument comprises a stylus having a tip and at least one second marker, and the pose of the secondary patient tracker is monitored while the tip of the stylus contacts the touchpoint.

XL. The method of any one of clauses XXXIII-XXXIX, wherein the first anatomic structure and the second anatomic structure comprise different vertebral levels of a spine of the patient.

XLI. The method of any one of clauses XXXIII-XL, wherein the secondary patient tracker does not include a second marker.

XLII. A computer-assisted surgery system, comprising:

a patient marker system comprising:
  a primary patient tracker having at least one radiological marker and at least one second marker and configured to attach to a first anatomic structure of a patient; and
  a secondary patient tracker having at least one radiological marker and configured to attach to a second anatomic structure of the patient;

a tracked instrument;

a motion tracking system configured to track the primary patient tracker and the instrument; and a computing device being configured to:
  obtain a three-dimensional image of a patient's anatomy and the primary patient tracker and the secondary patient tracker;
  identify locations of the radiological markers within a scan volume of the three-dimensional image;
  track a pose of the at least one second marker of the primary patient tracker in three-dimensional space using the motion tracking system while the primary patient tracker remains attached to the first anatomic structure;
  register the three-dimensional image of the patient's anatomy in three-dimensional space based on a known geometric relationship between the at least one radiological marker and the at least one second marker of the primary patient tracker;
  monitor the pose of the secondary patient tracker by tracking a tracked instrument located adjacent to the secondary patient tracker in three-dimensional space using the motion tracking system to determine whether the second anatomic structure has moved relative to the first anatomic structure; and
  provide feedback to a user of the computer-assisted surgery system based on a determination of movement of the second anatomic structure relative to the first anatomic structure.

XLIII. A patient marker system, comprising:

a primary patient tracker having at least one radiological marker and at least one second marker and configured to attach to a first anatomic structure of a patient; and a secondary patient tracker having at least one radiological marker and a touchpoint and configured to attach to a second anatomic structure of the patient.

XLIV. A method of registering patient images in a surgical system, comprising:

obtaining a three-dimensional image of a patient's anatomy and a patient tracker attached to the patient, the patient tracker comprising at least one hybrid marker having a radiological marker contained within an optical marker;

identifying a three-dimensional portion the hybrid marker within a scan volume of the three-dimensional image;

determining a location of the hybrid marker within the scan volume based on the identified three-dimensional portion of the hybrid marker;

tracking the location of the hybrid marker in three-dimensional space using a motion tracking system while the patient tracker remains fixed to the patient; and registering the three-dimensional image of the patient's anatomy in three-dimensional space based on a known geometric relationship between the location of the hybrid marker within the scan volume and the location of the hybrid marker in three-dimensional space.

XLV. The method of clause XLIV, wherein the optical marker comprises a spherically-shaped portion with a reflective coating over the spherically-shaped portion.

XLVI. The method of any one clauses XLIV or XLV, wherein the radiological marker is located at a centroid of the optical marker.

XLVII. The method of any one of clauses XLIV-XLVI, wherein obtaining a three-dimensional image of a patient's anatomy comprises performing a scan of the patient using an imaging device.

XLVIII. The method of any one of clauses XLIV-XLVII, further comprising detecting the hybrid marker with a localizer including an array of cameras to enable continuous real-time tracking of the patient tracker in three-dimensional space.

XLIX. The method of any one of clauses XLIV-XLVIII, further comprising controlling a surgical robot to move at least one of a robotic arm and end effector of the surgical robot to a pose in three-dimensional space relative to a location of an anatomical feature of the patient or the location of the hybrid marker that is identified within the scan volume of the three-dimensional image of the patient's anatomy.

L. The method of clause XLIX, further comprising monitoring the pose of the robotic arm by tracking a robot tracker, attached to the robotic arm, in three-dimensional space using the motion tracking system to determine whether the robot tracker moved relative to the hybrid marker; and adjusting the pose of the robotic arm based on a determination of movement of the robot tracker relative to at least one of the anatomical feature and hybrid marker.

LI. The method of any one of clauses XLIV-L, wherein determining the location of the hybrid marker within the scan volume based on the identified three-dimensional portion of the hybrid marker comprises finding a centroid of the three-dimensional portion of the hybrid marker.

LII. The method of any one of clauses XLIV-LI, wherein the radiological marker and the optical marker are separate components wherein the radiological marker is configured to be placed within the optical marker.

LIII. The method any one of clauses XLIV-LII, wherein the optical marker comprises a thermoplastic material that is doped with radiopaque material.

LIV. The method of any one of clauses LII or LIII, wherein the radiopaque material comprises at least one of barium, bismuth subcarbonate, barium sulfate, bismuth oxychloride, bismuth trioxide, tungsten and tantalum.

LV. The method of any one of clauses XLIV-LIV, wherein the at least one radiological marker comprises a discrete element comprised of radiopaque material having at least one dimension between 0.5 and 5 mm.

LVI. The method of any one of clauses XLIV-LV, wherein the hybrid marker comprises a light emitting source.

LVII. The method of any one of clauses XLIV-LVI, further comprising:

displaying image data of the patient's anatomy and the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

LVIII. The method of any one of clauses XLIV-LVII, further comprising:

storing data representing the known geometric relationship between at least one radiological marker and at least one optical marker of the patient tracker in a memory of a computing device connected with the surgical system.

LIX. The method of clause LVIII, wherein the data representing the known geometric relationship is stored in the memory of the computing device during a registration process that includes at least one of:

providing identifying data for the patient tracker to the computing device; and determining a geometric pattern of a plurality of hybrid markers of the patient tracker using the motion tracking system.

LX. A surgical system comprising:

a patient tracker attached to a patient, the patient tracker comprising at least one hybrid marker having a radiological marker contained within an optical marker;

a motion tracking system for tracking a location of the at least one hybrid marker; and a computing device being configured to:

obtain a three-dimensional image of a patient's anatomy and the patient tracker attached to the patient;

identify a three-dimensional portion of the hybrid marker within a scan volume of the three-dimensional image;

determine a location of the hybrid marker within the scan volume based on the identified three-dimensional portion of the hybrid marker;

track the location of the hybrid marker in three-dimensional space using the motion tracking system while the patient tracker remains fixed to the patient; and register the three-dimensional image of the patient's anatomy in three-dimensional space based on a known geometric relationship between the location of the hybrid marker within the scan volume and the location of the hybrid marker in three-dimensional space.

LXI. The surgical system of clause LX, wherein the optical marker comprises a spherically-shaped portion with a reflective coating over the spherically-shaped portion.

LXII. The surgical system of any one of clauses LX or LXI, wherein the radiological marker is located at a centroid of the spherically-shaped portion of the optical marker.

LXIII. The surgical system of any one of clauses LX-LXII, further comprising an imaging device for performing a scan of the patient to obtain the three-dimensional image of the patient's anatomy.

LXIV. The surgical system of any one of clauses LX-LXIII, wherein the motion tracking system includes a localizer for detecting the hybrid marker to enable continuous real-time tracking of the patient tracker in three-dimensional space.

LXV. The surgical system of clause LXIV, wherein based on the continuous real-time tracking of the patient tracker, the motion tracking system generates the three-dimensional space in a common coordinate system.

LXVI. The surgical system of any one of clauses LXIV or LXV, wherein based on the three-dimensional image of the patient's anatomy and the continuous real-time tracking of the patient tracker, the computing device is further configured to register the location of the hybrid marker in three-dimensional space.

LXVII. The surgical system of any one of clauses LX-LXVI, wherein determining the location of the hybrid marker within the scan volume based on the identified three-dimensional portion of the hybrid marker comprises finding a centroid of the hybrid marker.

LXVIII. The surgical system any one of clauses LX-LXVII, wherein the hybrid marker comprises a thermoplastic material that is doped with radiopaque material.

LXIX. The surgical system of clause LXVIII, wherein the radiopaque material comprises at least one of barium, bismuth subcarbonate, barium sulfate, bismuth oxychloride, bismuth trioxide, tungsten and tantalum.

LXX. The surgical system of any one of clauses LX-LXIX, wherein the hybrid marker comprises a light emitting source.

LXXI. The surgical system of any one of clauses LX-LXX, further comprising a surgical robot including a robotic arm and an end effector coupled to the robotic arm.

LXXII. The surgical system of clause LXXI, wherein the surgical robot further includes a controller that is configured to move at least one of the robotic arm and end effector to a pose in three-dimensional space relative to the location of an anatomical feature of the patient or the location of the hybrid marker that is identified within the scan volume of the three-dimensional image of the patient's anatomy.

LXXIII. The surgical system of any one of clauses LXXI or LXXII, wherein the computing device is further configured to:
monitor the pose of the robotic arm by tracking a robot tracker, attached to the robotic arm, in three-dimensional space using the motion tracking system to determine whether the robot tracker moved relative to the hybrid marker; and
adjust the pose of the robotic arm based on a determination of movement of the robot tracker relative to at least one of the anatomical feature and hybrid marker.

LXXIV. The surgical system of any one of clauses LX-LXXIII, wherein the computing device is further configured to display image data of the patient's anatomy obtained by the imaging device and the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

LXXV. The surgical system of any one of clauses LX-LXXIV, wherein the computing device is further configured to store data representing the known geometric relationship between at least one radiological marker and at least one optical marker of the patient tracker in a memory of the surgical system.

LXXVI. The surgical system of clause LXXV, wherein the data representing the known geometric relationship is stored in the memory of the surgical system during a registration process that includes at least one of:
providing identifying data for the patient tracker to the computing device of the surgical system; and
determining a geometric pattern of a plurality of hybrid markers of the patient tracker using the motion tracking system.

LXXVII. A surgical system, comprising:
a patient tracker attached to a patient, the patient tracker comprising at least one hybrid marker having a radiological marker contained within an optical marker;
a motion tracking system for tracking a location of the at least one hybrid marker;
an imaging device configured to perform a scan of the patient while the patient tracker is attached to the patient; and
a computing device being configured to:
obtain a three-dimensional image of a patient's anatomy and the patient tracker attached to the patient;
identify a three-dimensional portion of the hybrid marker within a scan volume of the three-dimensional image;
determine a location of the hybrid marker within the scan volume based on the identified three-dimensional portion;
track the location of the hybrid marker in three-dimensional space using the motion tracking system while the patient tracker remains fixed to the patient; and
register the three-dimensional image of the patient's anatomy in three-dimensional space based on a known geometric relationship between the location of the hybrid marker within the scan volume and the location of the hybrid marker in three-dimensional space.

LXXVIII. The surgical system of clause LXXVII, wherein the optical marker comprises a spherically-shaped portion with a reflective coating over the spherically-shaped portion.

LXXIX. The surgical system of any one of clauses LXXVII or LXXVIII, wherein the radiological marker is located at a centroid of the spherically-shaped portion of the optical marker.

LXXX. The surgical system of any one of clauses LXXVII-LXXIX, further comprising a surgical robot including a robotic arm and an end effector coupled to the robotic arm.

LXXXI. The surgical system of clause LXXX, wherein the surgical robot further includes a controller that is configured to move at least one of the robotic arm and end effector to a pose in three-dimensional space relative to the location of an anatomical feature of the patient that is identified within the scan volume of the three-dimensional image of the patient's anatomy.

LXXXII. The surgical system of any one of clauses LXXX or LXXXI, wherein the surgical robot is configured to couple to the imaging device.

LXXXIII. The surgical system of any one of clauses LXXVII-LXXXII, wherein the motion tracking system includes a localizer having an array of cameras.

LXXXIV. The surgical system of clause LXXXIII, wherein the localizer is configured to detect the optical marker of the hybrid marker to enable continuous real-time tracking of the patient tracker in three-dimensional space.

LXXXV. The surgical system of any one of clauses LXXXIII or LXXXIV, wherein the localizer is mounted to a rigid support and the rigid support, including the localizer, is suspended above a surgical area and a pose of the rigid support is adjustable with respect to a robotic arm and the imaging device.

LXXXVI. The surgical system of any one of clauses LXXX-LXXXII, wherein the computing device is further configured to:
monitor the pose of the robotic arm by tracking a robot tracker, attached to the robotic arm, in three-dimensional space using the motion tracking system to determine whether the robot tracker moved relative to the hybrid marker;
adjust the pose of the robotic arm based on a determination of movement of the robot tracker relative to at least one of the anatomical feature and hybrid marker.

LXXXVII. The surgical system of any one of clauses LXXVII-LXXXVI, wherein the computing device is further configured to display image data of the patient's anatomy obtained by the imaging device and the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

LXXXVIII. A surgical system, comprising:
a patient tracker attached to a patient, the patient tracker comprising at least one hybrid marker having a radiological marker contained within an optical marker;
a surgical robot including a robotic arm and an end effector, the robotic arm includes a robot tracker attached to the robotic arm;
a motion tracking system for tracking a location of the at least one hybrid marker and a location of the robot tracker;
an imaging device configured to perform a three-dimensional image scan of the patient while the patient tracker is attached to at least one anatomical feature of the patient; and
a computing device being configured to:
track the location of the hybrid marker in three-dimensional space using the motion tracking system while the patient tracker remains attached to the patient;
track the location of the robot tracker in three-dimensional space using the motion tracking system while the robot track remains attached to the robotic arm;
monitor a pose of the robotic arm by tracking the robot tracker in three-dimensional space using the motion tracking system to determine whether the robot tracker moved relative to the hybrid marker; and
adjust the pose of the robotic arm based on a determination of a movement of the robot tracker relative to at least one of anatomical feature and hybrid marker.

LXXXIX. The surgical system of clause LXXXVIII, wherein the surgical robot further includes a controller that is configured to move at least one of the robotic arm and the end effector to a pose in three-dimensional space relative to the location of an anatomical feature of the patient that is identified within a scan volume of the three-dimensional image of the patient.

XC. The surgical system of any one of clauses LXXXVIII or LXXXIX, wherein the optical marker comprises a spherically-shaped portion with a reflective coating over the spherically-shaped portion.

XCI. The surgical system of any one of clauses LXXXVIII-XC, wherein the radiological marker is located at a centroid of the spherically-shaped portion of the optical marker.

XCII. The surgical system of any one of clauses LXXXVIII-XCI, wherein the surgical robot is configured to couple to the imaging device.

XCIII. The surgical system of any one of clauses LXXXVIII-XCII, wherein the motion tracking device includes a localizer. for tracking the location of the hybrid marker in three-dimensional space.

XCIV. The surgical system of clause XCIII, wherein the localizer is configured to track the location of the hybrid marker in three-dimensional space while the patient tracker remains attached to the patient.

XCV. The surgical system of any one of clauses LXXXVIII-XCIV, wherein the computing device is further configured to:
obtain a three-dimensional image of a patient's anatomy and the patient tracker attached to the patient;
identify a three-dimensional portion of the hybrid marker within a scan volume of the three-dimensional image; and
determine the location of the hybrid marker within the scan volume based on the identified three-dimensional portion of the hybrid marker.

XCVI. The surgical system of any one of clauses LXXXVIII-XCV, wherein the computing device is further configured to display image data of the patient's anatomy obtained by the imaging device and the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

What is claimed is:
1. A surgical system comprising:
a patient tracker adapted for attachment to a patient, the patient tracker comprising at least one hybrid marker having:
an optical marker having a reflective coating, and
a radiological marker contained within the optical marker, the radiological marker having a spherical profile;
an upper portion defining the optical marker, a lower portion extending from the upper portion and defining an inlet, and an internal open portion defined extending from the inlet through the lower portion and into the upper portion to define a tapered channel, wherein the inlet is shaped to receive the radiological marker along the internal open portion and into the tapered channel, with the tapered channel terminating adjacent to a geometric center of a generally spherical profile of the optical marker and shaped to retain the radiological marker within a closed end of the tapered channel in a position substantially coincident with the geometric center of the generally spherical profile;

a motion tracking system for tracking a location of the at least one hybrid marker; and a computing device being configured to:
obtain a three-dimensional image of a patient's anatomy and the patient tracker attached to the patient;
identify a three-dimensional portion of the radiological marker within a scan volume of the three-dimensional image;
determine a location of the hybrid marker within the scan volume based on the identified three-dimensional portion of the radiological marker;
track the location of the optical marker in three-dimensional space using the motion tracking system while the patient tracker remains fixed to the patient; and
register the three-dimensional image of the patient's anatomy in three-dimensional space based on a known geometric relationship between the location of the radiological marker within the scan volume and the location of the optical marker in three-dimensional space;

wherein the radiological marker defines a first diameter, and the optical marker has a spherical profile defining a second diameter larger than the first diameter.

2. The surgical system of claim 1, wherein the optical marker comprises a spherically-shaped portion with the reflective coating over the spherically-shaped portion.

3. The surgical system of claim 2, wherein the radiological marker is located at a centroid of the spherically-shaped portion of the optical marker.

4. The surgical system of claim 1, further comprising an imaging device for performing a scan of the patient to obtain the three-dimensional image of the patient's anatomy.

5. The surgical system of claim 1, wherein the motion tracking system includes a localizer for detecting the optical marker to enable continuous real-time tracking of the patient tracker in three-dimensional space.

6. The surgical system of claim 5, wherein based on the continuous real-time tracking of the patient tracker, the motion tracking system generates the three-dimensional space in a common coordinate system.

7. The surgical system of claim 6, wherein based on the three-dimensional image of the patient's anatomy and the continuous real-time tracking of the patient tracker, the computing device is further configured to register the location of the hybrid marker in three-dimensional space.

8. The surgical system of claim 1, wherein the computing device is further configured to find a centroid of the radiological marker determine the location of the hybrid marker within the scan volume based on the identified three-dimensional portion of the radiological marker comprises finding a centroid of the hybrid marker.

9. The surgical system of claim 1, wherein the radiological marker comprises a thermoplastic material that is doped with radiopaque material.

10. The surgical system of claim 9, wherein the radiopaque material comprises at least one of barium, bismuth subcarbonate, barium sulfate, bismuth oxychloride, bismuth trioxide, tungsten and tantalum.

11. The surgical system of claim 1, further comprising a surgical robot including a robotic arm and an end effector coupled to the robotic arm.

12. The surgical system of claim 11, wherein the surgical robot further includes a controller configured to operate the robotic arm to place the end effector in a pose in three-dimensional space relative to the location of the radiological marker identified within the scan volume of the three-dimensional image of the patient's anatomy.

13. The surgical system of claim 12, further comprising a robot tracker operatively attached to the robotic arm; and
wherein the computing device is further configured to monitor the pose of the robotic arm by tracking the robot tracker in three-dimensional space using the motion tracking system to determine movement of the robot tracker relative to the hybrid marker; and
wherein the controller of the surgical robot is further configured to adjust the pose of the robotic arm based on a determination of movement of the robot tracker relative to the hybrid marker.

14. The surgical system of claim 4, wherein the computing device is further configured to display image data of the patient's anatomy obtained by the imaging device and the three-dimensional image of the patient's anatomy on a display device, where the three-dimensional image is augmented by a graphical representation of at least one additional object that is tracked by the motion tracking system in the same three-dimensional space in which the three-dimensional image of the patient's anatomy is registered.

15. The surgical system of claim 1, wherein the computing device is further configured to store data representing the known geometric relationship between the radiological marker and the optical marker of the patient tracker in a memory of the surgical system.

16. The surgical system of claim 15, wherein the data representing the known geometric relationship is stored in the memory of the surgical system during a registration process.

17. The surgical system of claim 1, wherein the radiological marker comprises radiopaque sapphire material.

18. The surgical system of claim 1, wherein a ratio of the second diameter relative to the first diameter is at least 3:1.

* * * * *